US011024420B2

(12) United States Patent
Shimomura et al.

(10) Patent No.: US 11,024,420 B2
(45) Date of Patent: Jun. 1, 2021

(54) METHODS AND APPARATUS FOR LOGGING INFORMATION USING A MEDICAL IMAGING DISPLAY SYSTEM

(71) Applicant: FUJIFILM MEDICAL SYSTEMS U.S.A., INC., Lexington, MA (US)

(72) Inventors: Takuya Shimomura, Cary, NC (US); Tatsuo Kawanaka, Cary, NC (US); Keiji Sugihara, Morrisville, NC (US)

(73) Assignee: FUJIFILM MEDICAL SYSTEMS U.S.A., INC., Lexington, MA (US)

( * ) Notice: Subject to any disclaimer, the term of this patent is extended or adjusted under 35 U.S.C. 154(b) by 653 days.

(21) Appl. No.: 14/820,144

(22) Filed: Aug. 6, 2015

(65) Prior Publication Data
US 2017/0039320 A1 Feb. 9, 2017

(51) Int. Cl.
*G16H 40/63* (2018.01)
*G16H 10/60* (2018.01)
(Continued)

(52) U.S. Cl.
CPC ............ *G16H 40/63* (2018.01); *G16H 10/60* (2018.01); *G16H 30/20* (2018.01); *G16H 30/40* (2018.01); *G16H 50/70* (2018.01)

(58) Field of Classification Search
CPC ........ G06Q 50/22; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70;
(Continued)

(56) References Cited

U.S. PATENT DOCUMENTS

2008/0031503 A1* 2/2008 Kanada ................. G06F 19/321
382/128
2011/0179094 A1* 7/2011 Noordvyk ............. G06F 19/321
707/821
(Continued)

FOREIGN PATENT DOCUMENTS

JP 2009230304 10/2009
JP 2012501015 1/2012
(Continued)

OTHER PUBLICATIONS

Jacob, Robert J.K., "A specification language for direct-manipulation user interfaces," 1986, ACM Transactions on Graphics, vol. 5, No. 4, pp. 283-317. (Year: 1986).*
(Continued)

*Primary Examiner* — Lena Najarian
(74) *Attorney, Agent, or Firm* — Heslin Rothenberg Farley & Mesiti P.C.

(57) ABSTRACT

A method and apparatus for logging information using a medical image display system. In one embodiment, the method comprises accessing a first medical study; displaying one or more images from the first medical study in a first display area of a screen; receiving one or more user inputs related to a user's interactions with the first display area; receiving a user input to add a first selectable entry into a list of one or more entries displayed in a second display area; adding the first selectable entry to the list in response to receiving a user input; and storing the list for future access with the first medical study.

39 Claims, 19 Drawing Sheets

(51) Int. Cl.
  *G16H 50/70* (2018.01)
  *G16H 30/20* (2018.01)
  *G16H 30/40* (2018.01)

(58) Field of Classification Search
  CPC ........ G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
  See application file for complete search history.

(56) References Cited

U.S. PATENT DOCUMENTS

| | | | |
|---|---|---|---|
| 2012/0159324 A1* | 6/2012 | Chavez | G06Q 50/24 715/704 |
| 2013/0103417 A1 | 4/2013 | Seto | |
| 2014/0157288 A1* | 6/2014 | Wong | G06F 11/3476 719/318 |
| 2015/0265233 A1* | 9/2015 | Aoyagi | G06F 17/30277 345/635 |
| 2017/0140105 A1* | 5/2017 | Smith | G06F 19/322 |

FOREIGN PATENT DOCUMENTS

| | | |
|---|---|---|
| JP | 2012027565 | 2/2012 |
| JP | 2013152699 | 8/2013 |
| JP | 2014023687 | 2/2014 |
| WO | WO 2010/022375 | 2/2010 |
| WO | 2012002287 | 1/2012 |

OTHER PUBLICATIONS

Japanese Office Action for Application No. 2016154164 dated Apr. 9, 2020, 10 pages.

Translation of First Office action of Japan Patent Office, of corresponding JP application No. 2016-154164 "Methods and Apparatus for Logging Information Using Medical Imaging Display System" dated May 9, 2020.

* cited by examiner

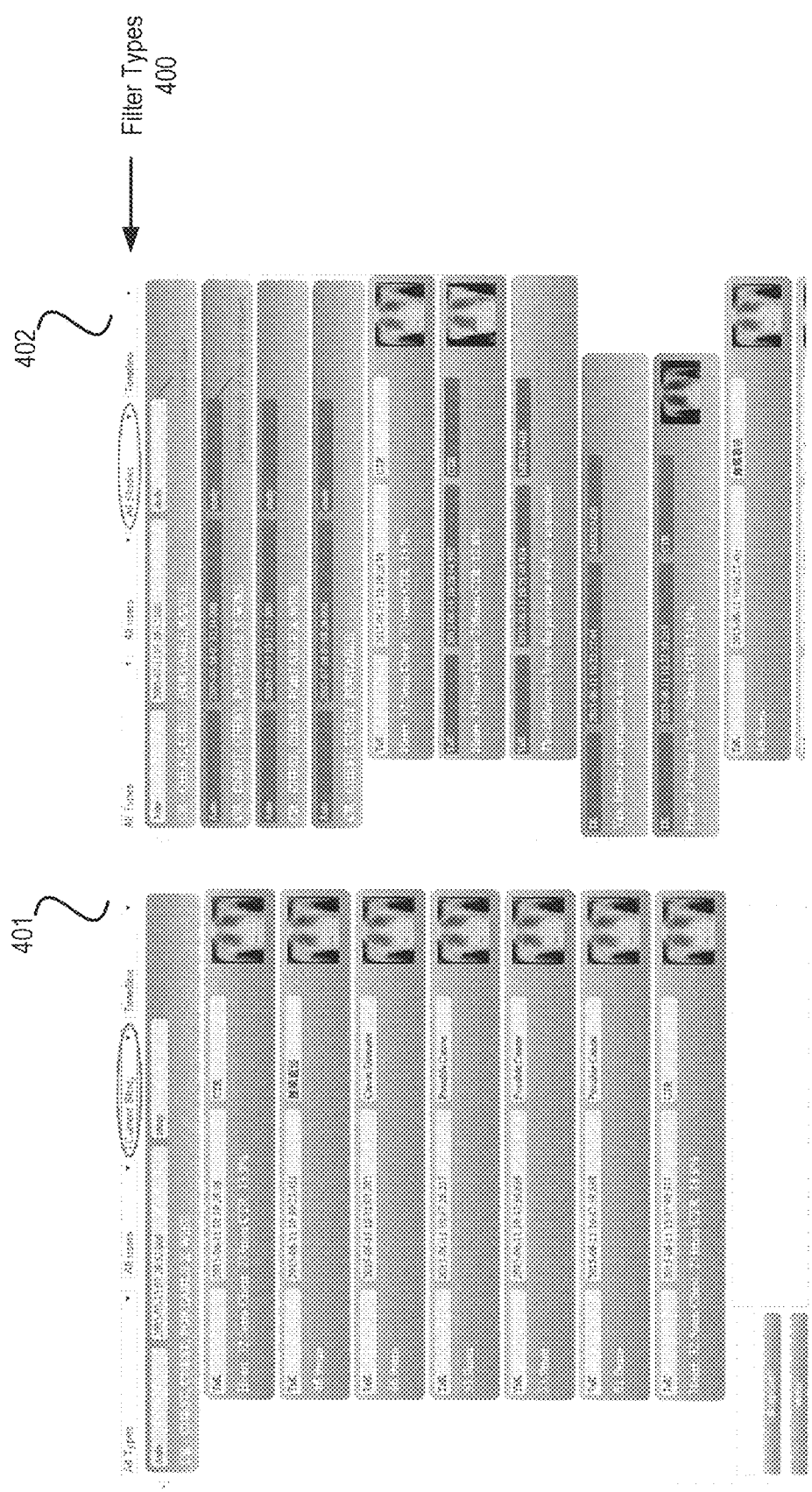

1st study

2nd study

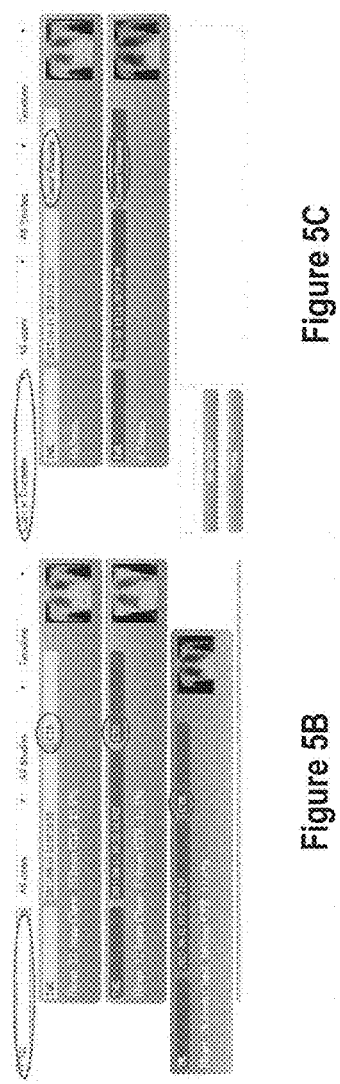
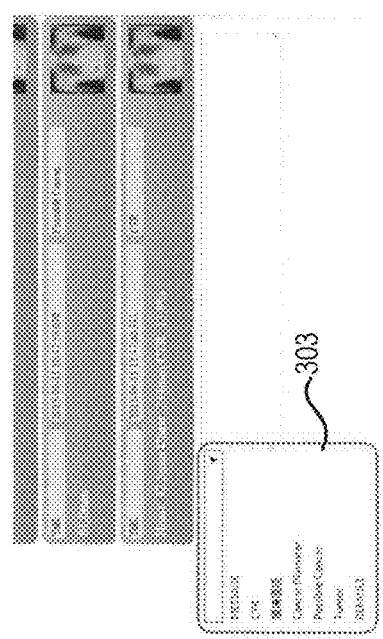
Figure 5C
Figure 5B
Figure 5A

METHODS AND APPARATUS FOR LOGGING INFORMATION USING A MEDICAL IMAGING DISPLAY SYSTEM

FIELD

Embodiments of the disclosure relate to improving the display of medical images and information relevant to one or more of the displayed medical images. More specifically, embodiments of the disclosure relate to creating log entries for a log with information related to medical studies, including generating a snapshot of one or more states of a display of medical images and the information relevant to the displayed medical images and storing such information as part of the log entries.

GENERAL BACKGROUND

Current medical imaging technology includes the use of medical images such as, among others, x-rays, mammograms, computerized tomography (CT) scans, magnetic resonance images (MRIs), positron emission tomography (PET) scans and ultrasound images. Some medical facilities, such as doctors' offices, dentists' offices, hospitals, etc., may use x-ray illuminators to view physical printouts of medical images. However, medical facilities are beginning to adopt electronic displays for displaying medical images.

As medical facilities adopt electronic displays, medical personnel, such as doctors, nurses or medical technicians, have difficulty accessing a plurality of pieces of medical information at once. Previously, with x-ray illuminators, for example, a plurality of physical x-ray image films may be hung against a backlit screen of an x-ray illuminator. Additionally, medical personnel had the ability to hang other relevant medical information, such as medical records, charts, surgery procedures, etc., in a side-by-side manner with one or more x-rays.

Upon adopting electronic displays to display medical information, medical personnel are required to open a separate display screen for each piece of medical information. This requires the medical personnel explaining the medical information to continually switch amongst the open windows, which is often clumsy and confusing for the medical personnel as well as for the viewer. For example, a doctor may be explaining an injury using a plurality of x-rays to a patient. By switching between the plurality of open windows, one for each x-ray, it is foreseeable that the doctor and patient may become confused, or the patient might not fully understand the injury and the potential treatment options as a result.

However, one advantage of switching to electronic displays is that adjusting viewing properties for one or more medical images has become easier (e.g., attributes of the one more medical images). For example, adjusting the brightness level of an image on a computer for display on the display screen is easier and more convenient than adjusting the light source of an x-ray illuminator. However, when medical personnel adjusts one or more viewing properties (e.g., zoom level, brightness level, contrast level, etc.) of one or more medical images in order to draw a conclusion on the injury and/or treatment required, the medical personnel is required to recall the adjustments the next time the one or more medical images are displayed. For example, when a doctor increases a zoom level and then increases a contrast level on an x-ray in order to determine, for example, that a fracture is present in the ulna of the patient's left hand, the doctor will have to recall the amount of increase in the zoom level and contrast level when illustrating the fracture to the patient or to a surgeon. Additionally, the doctor may also have to recall the arrangement of a second medical image (or other medical information) that was used in drawing a conclusion regarding the fracture and/or possible treatment options. In some instances, a particular viewing arrangement, e.g., a side-by-side comparison of two medical images having different perspectives of an injury wherein one or more of the medical images have had viewing properties adjusted, may be critical in seeing the injury.

Furthermore, relaying information as to how to adjust the viewing properties and a particular arrangement of medical information to medical personnel located remotely from the medical personnel creating the arrangement is very difficult. For example, if a doctor in California is examining a patient with severe head trauma and would like a second opinion of the diagnosis from the foremost expert in head trauma, who happens to be at a hospital in France, it would be very difficult, currently, for the doctor in California to relay information as to how the medical information (images, notes, medical records, etc.) should be arranged and how the viewing properties of one or more of the medical images should be adjusted.

In other words, when a physician wants to perform a collaborative reading of a study with one or more other physicians or support and respond to inquiries from those physicians, the other physicians would often have to repeat the same operations that were performed during the previously review of a study to have the other individuals see the same type of information related to the study. Thus, because there is no way to preserve or retrieve a display state in a viewer effectively, physicians can only collaborate with each other in real time for it to be effective. This forces them to stop what they are currently working on and engage the other doctor, thereby causing an interruption with respect to their current activity, which may be with another patient.

Therefore, it would be advantageous to have a method of recording a user's interactions with a display screen as well as record their comments to save the information, including the preservation of any adjusted viewing properties, such that the saved state and save comments may be easily recalled in the future.

SUMMARY

A method and apparatus for logging information using a medical image display system. In one embodiment, the method comprises accessing a first medical study; displaying one or more images from the first medical study in a first display area of a screen; receiving one or more user inputs related to a user's interactions with the first display area; receiving a user input to add a first selectable entry into a list of one or more entries displayed in a second display area; adding the first selectable entry to the list in response to receiving a user input; and storing the list for future access with the first medical study.

BRIEF DESCRIPTION OF THE DRAWINGS

The disclosure may best be understood by referring to the following description and accompanying drawings that are used to illustrate embodiments of the disclosure.

FIGS. 4A and 4B illustrate a log user interface that includes filter types.

FIGS. 5A-C illustrate the log type assignment and filtering logs with different types.

DETAILED DESCRIPTION OF THE PRESENT INVENTION

Figure 1:
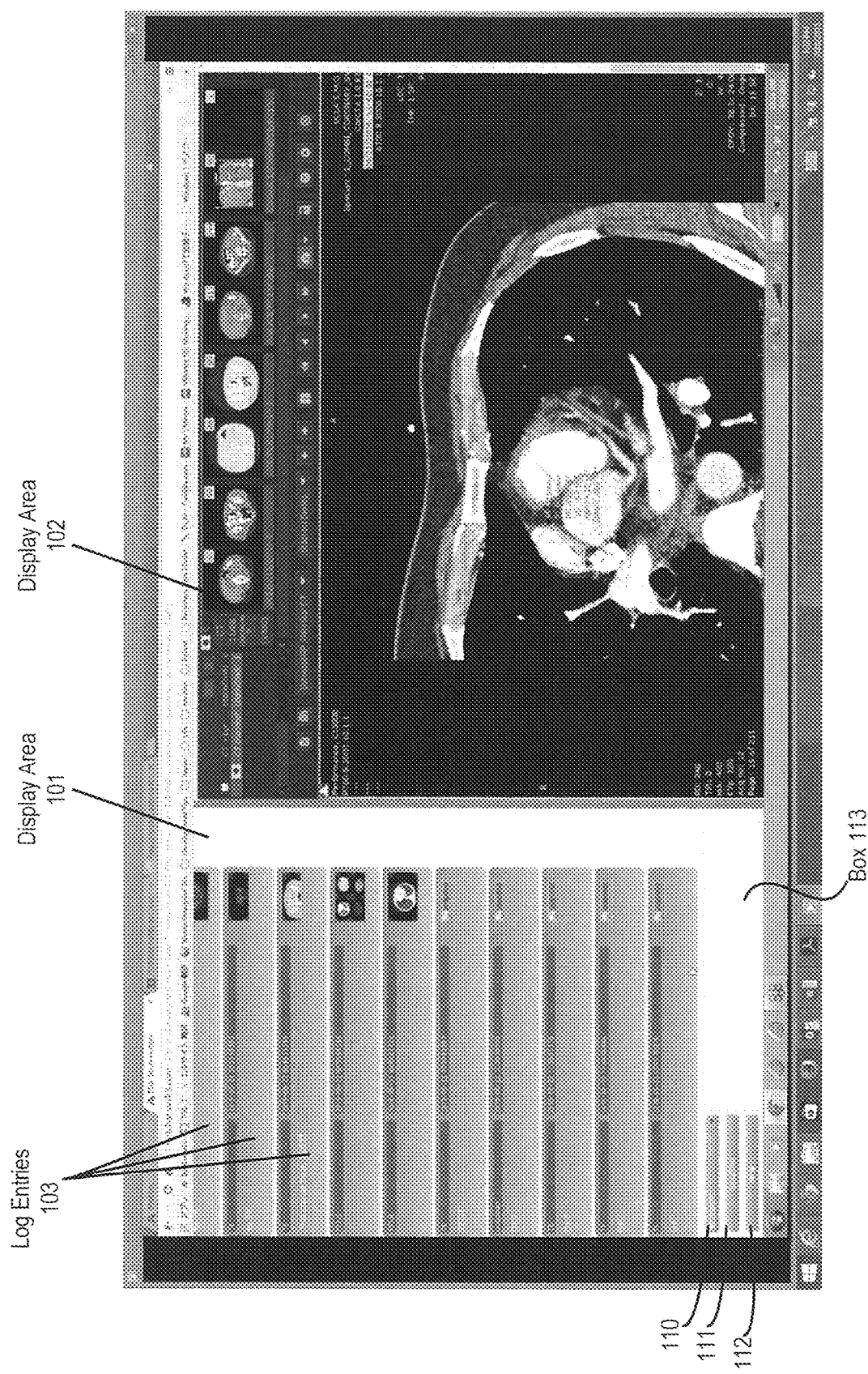
FIG. 1 illustrates an example of a user interface(s) that includes a log.

Various embodiments of the disclosure relate to creating a log that may be used to save comments and other text and alphanumeric data, along with the state of one or more user interface screens displaying medical images, and, optionally, information related to one or more of the displayed medical images when an individual reviews a study. By enabling a user to record their comments along with copies of user interface screens displaying medical images that were viewed while reviewing the study, the user is able to record their thinking process while reviewing the study.

Herein, the term "study" refers broadly to a compilation of medical information that may include a single medical image, a medical record or a set of medical notes, or may include one or more of a medical image, a medical record or a set of medical notes set forth in a design layout (e.g., a template). Additionally, one or more states of the design layout, including the content imported therein and any adjustments made to one or more display attributes, may be saved, wherein the grouping of one or more saved states may be referred to as a snapshot. For example, a first saved state may include a first medical image having a default brightness setting and a second saved state may include the first medical image having an adjusted brightness setting. Each of the one or more saved states may include an adjustment to one or more display attributes of the content of one or more of the display areas. As stated above, the grouping of the one or more saved states of the design layout may be referred to as a snapshot of the design layout.

Specifically, by enabling a user to save their comments along with the state of a layout, including the state of each adjusted medical image, the user may quickly recall a particular state of interest that is important to a diagnosis, presentation or is particularly unique. Herein, the term "adjusted image" may refer to a medical image that has had one or more viewing properties altered. Examples of viewing properties may include, but are not limited or restricted to, a zoom level, a brightness level, a contrast level, color settings, a positioning of the image, a rotation of the image, etc. It is desirable for the doctor to be able to save comments and the state of the layout, e.g., the exact layout comparing the two or more x-ray images and the previous medical history, so as to be able to return to the exact layout when discussing the injury or the appropriate procedure with the patient and/or medical staff. Herein, the term "snapshot" may be referred to as a grouping of one or more saved states of a particular layout.

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; etc.

Overview

A log for use in saving comments and captured display states (snapshots) is described. In one embodiment, the log is a set of entries created by a user depicting those comments and snapshots of the display on the screen. The entries are created by a user reviewing a medical study. In one embodiment, the study is selected from a work list. When opened, images or other information from the study are displayed on one portion of the screen and the log is displayed on another portion of the display screen. The portion of display screen showing contents from the study may have one or more different display areas and/or different display windows.

In one embodiment, the log resembles some of the thinking processes the user had during one or more previous reviews of the study. In other words, the log is a tool that allows individuals reviewing a study to store their thought process when reviewing a study, including capturing or recording of operations that they perform when interacting with the content in the study via a user interface. For example, the user may make annotations on images of the study, take measurements of items depicted in the images of the study and even generate conclusions (e.g., a diagnosis, a treatment plan, etc.). At any time while this is occurring, the user is able to create entries in the log that include notes (or other alphanumeric data) and/or take snapshots to capture the display state of the other display area of the display screen and store that into the log. Thus, this logging tool enables the accumulation of the user's knowledge with respect to the study.

In one embodiment, the user could review the log by scrolling through the entries. In one embodiment, one or more scroll bars are included in the user interface containing the log to enable a user to scroll through the log entries that are listed. In another embodiment, by moving a cursor in a particular direction, the user causes log entries that are not shown to be shown. For example, by moving the cursor on the display screen up to a certain position of the user interface displaying the log (e.g., right above the top of the list of entries in the log), additional log entries at the top of the log that are not currently being displayed are then displayed.

By selecting an entry in the log, any snapshot captured and associated with the log entries is displayed in the other display area used to display study contents. At that point, the display area showing the snapshot is interactive and the user may interact with the display content that had been previously captured in the same fashion as had been done previously. For example, a user can take measurements or perform image processing operations (e.g., panning, zooming, etc.) on the images displayed from the snapshot. Furthermore, the user can create more log entries from those interactions and those new log entries can be added to the log. In such a case, any additional notes and/or captured display states can be added to the log. In one embodiment, these log entries are added into the log directly beneath (adjacent to) the entry that was selected and had its associated snapshot displayed on the screen. In another embodiment, the added entries are added to a particular point (e.g., the bottom) of the log. In this case, the log entries may include information that indicates the entry from which the new log entry is followed. In this manner, the user is allowed to continue their thinking process from that point into the log when they selected an entry. Also, the user is able to repeat the analysis from any mid-point in their previous review process by selecting an entry in the log and continuing from that point to interact with the study. This in essence starts a new thread in the log.

In one embodiment, the log may be searched to obtain specific information desirable to an individual. For example, the log may be searched by patient name, study number, procedure type, etc. to obtain a list of entries with the information that is sought by the individual performing the search.

In one embodiment, the log itself is added to the study. In one embodiment, this is performed using DICOM to send material to be added to the study. More specifically, in one embodiment, when a DICOM server receives a new study from a modality, a new log is created for the new study. Also in one embodiment, at that time a new log entry would be created to represent the study information. This entry is included in the log. In one embodiment, a reference or portion to the log is included in the study to enable the log to be located for display and/or modification when the study is being viewed. Therefore, in one embodiment, any individual accessing the study in the future can access the log to see what notes and/or any captured display states exist from past reviews which may be very useful to other individuals who may be able to use that information. For example, if a first doctor reviews a study and creates log entries based on their review, thereby depicting the steps that he or she took to arrive at a particular conclusion, another physician would be able to reviews those same steps by reviewing the log entries and their associated notes and snapshots and determine whether they agree or disagree with the conclusion made by the other doctor.

FIG. 1 illustrates an example of a user interface(s) that includes a log. Referring to FIG. 1, the user interface includes a display area 101 and display area 102. Each display area is a user interface itself. Display area 101 includes a log with log entries (e.g., log entries 103). In one embodiment, display area also includes message button 110, snapshot button 111 and write button 112, along with log entry creation box 113. When a user opens one or more studies, content from the studies are displayed in display area 102. An individual may interact with display area 102 and perform a number of different functions.

Log entries can include notes, memos or other text entered by a user. The log entries may also include a snapshot of display area 102. In this case, the snapshot of display area 102 is a captured display state that will be associated with the log entry. Note that in one embodiment, this captured display state of the snapshot is stored with the log entry. In another embodiment, the reference or pointer to a memory location containing the display state is included in the log entry.

When creating a log entry, a user clicks on message button 110 to choose the type of log entry. If the user wishes to add a snapshot to the log entry, the user selects snapshot button 111. When the user selects snapshot 111, the state of the display in display area 102 is captured for the log entry. Note that display area 102 may include one or more windows displaying different portions (e.g., images) of a study or portions of different studies or other material such as, for example, reports, documents (PDF, Microsoft Word, image etc.). Once the user has entered whatever message information and the snapshot into a log entry, user presses write button 112 to add the log entry to the log.

Figure 2:
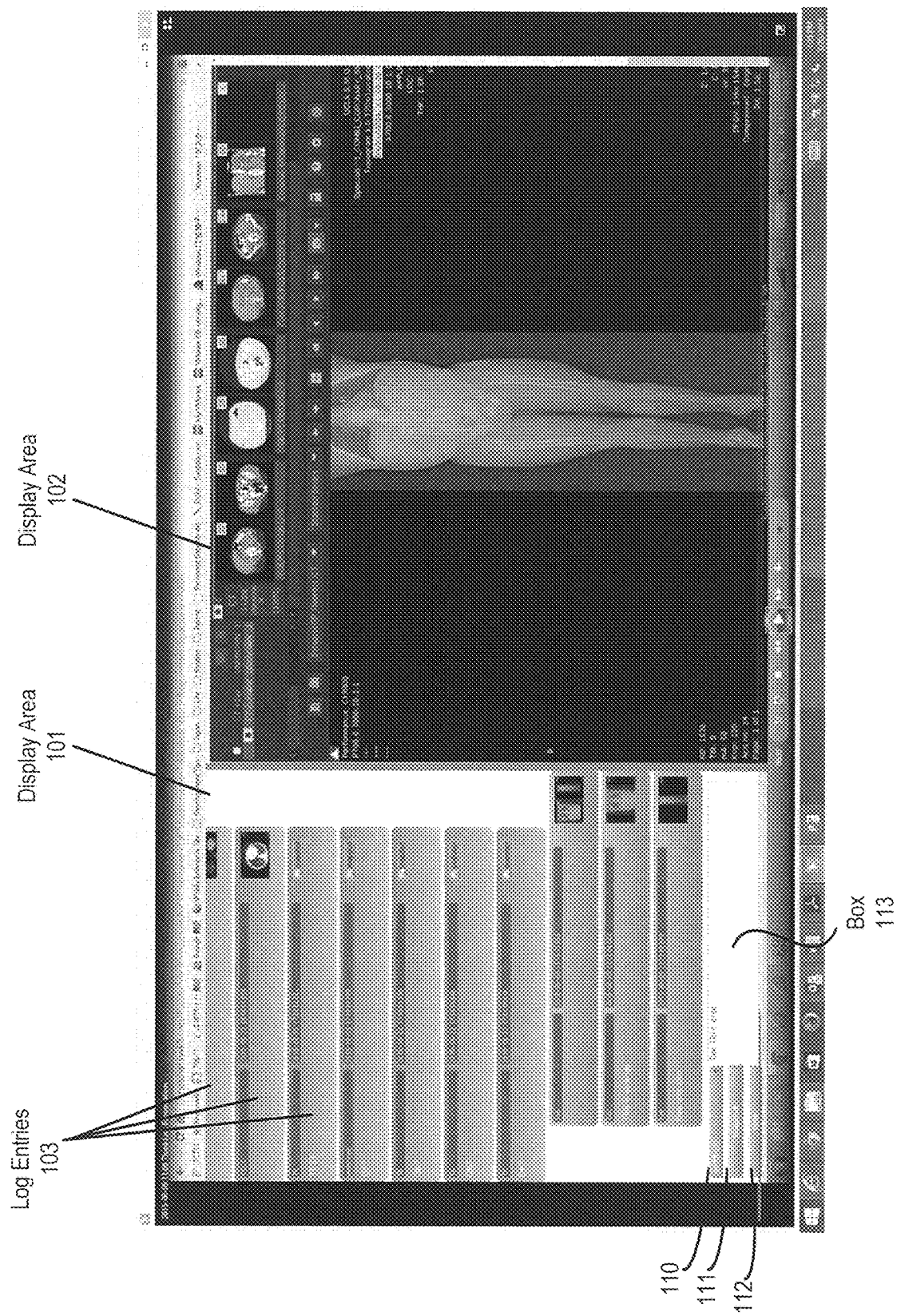
FIG. 2 illustrates an example of text being written into a box.

FIG. 2 illustrates an example of text being written into box 113. Referring to FIG. 2, box 113 allows entry of text before the user clicks on the message button 112. When button 112 is clicked, text in box 113 is added to a new log entry with the type selected in message button 110 and snapshot obtained by clicking button 111 (if a snapshot exists).

Figure 3A:
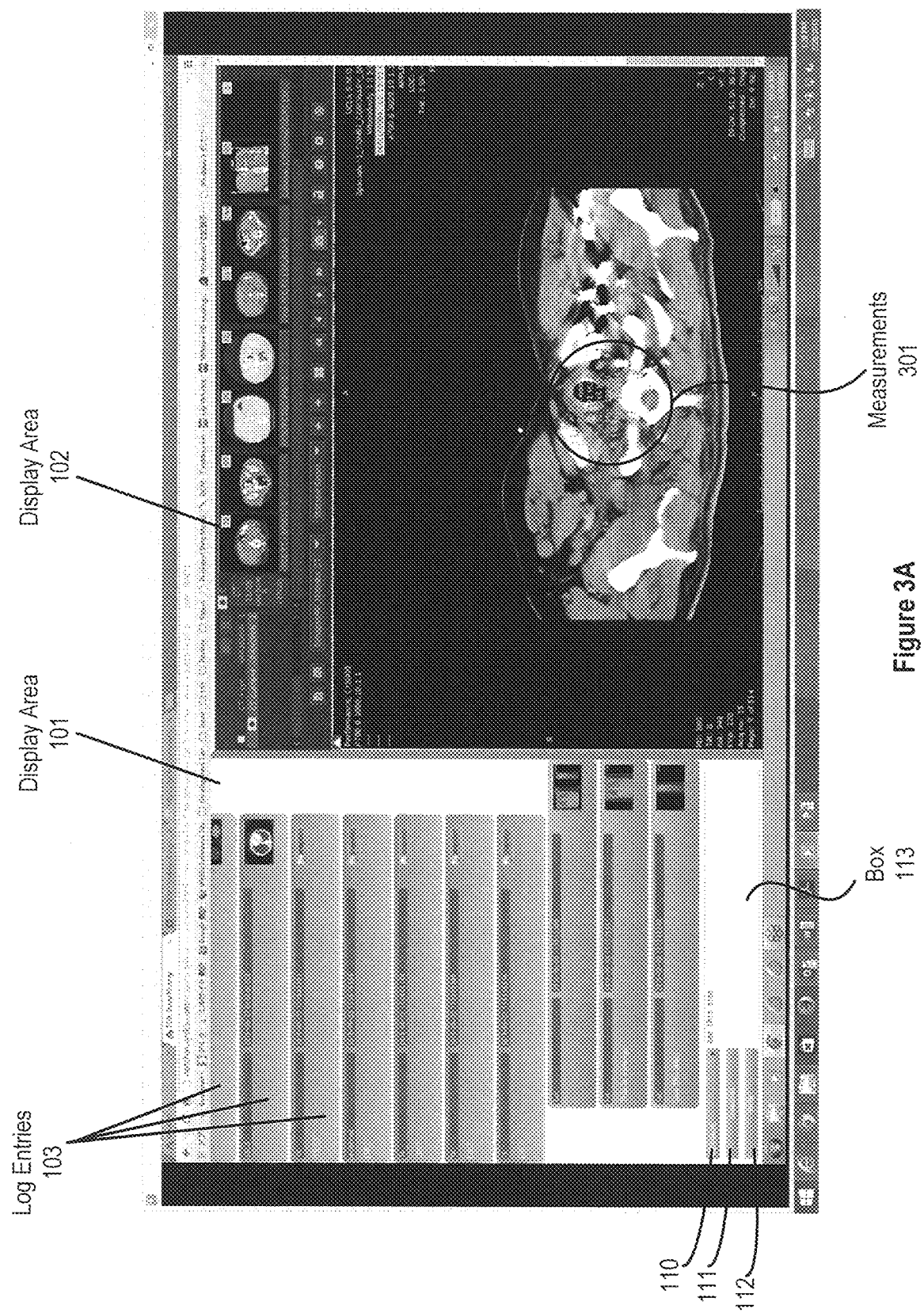
FIGS. 3A-3C illustrate text from an image display area automatically being added to a log entry.
Figure 3B:
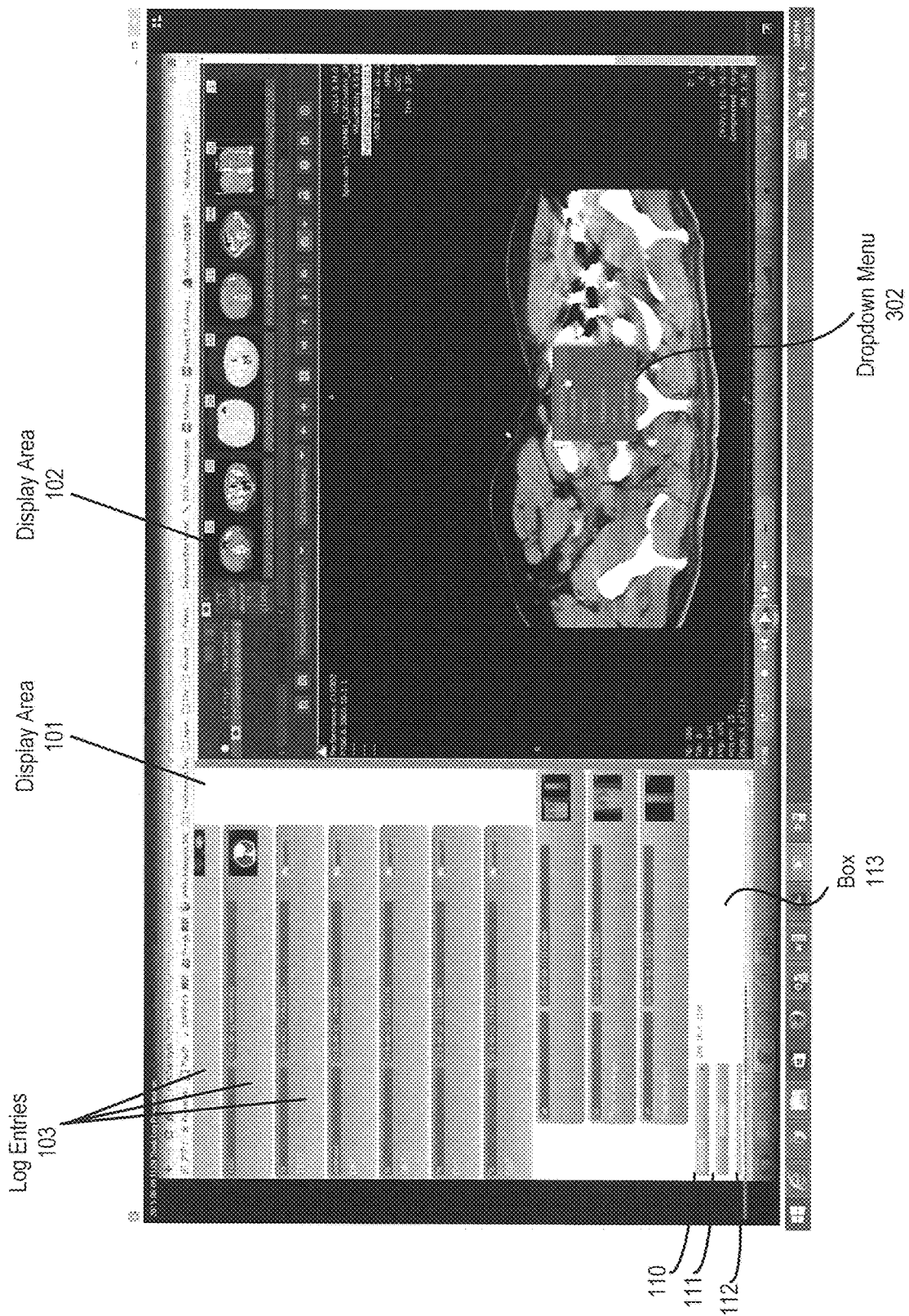
Figure 3C:
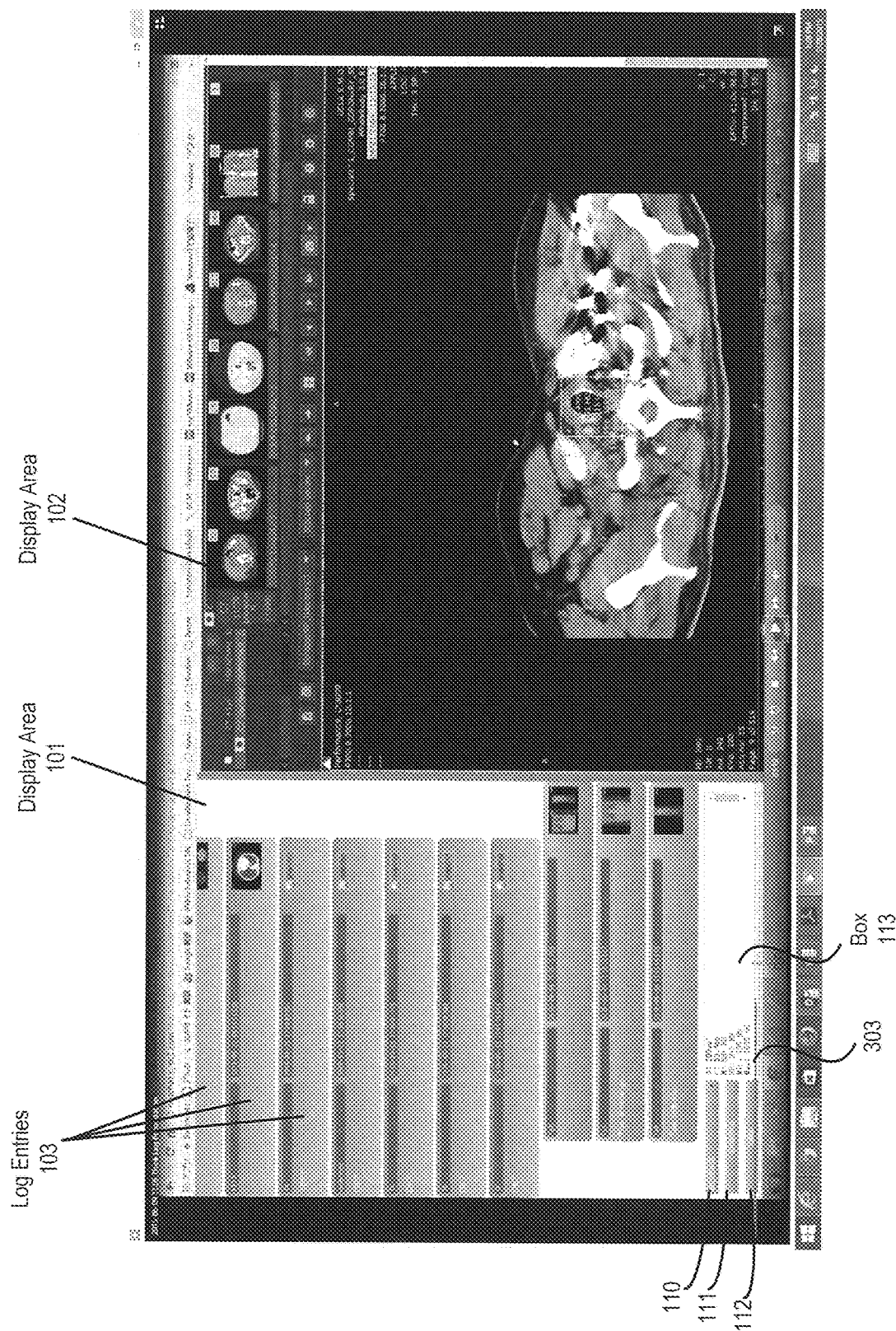

In one embodiment, text information and other annotations that appear in display window 102 may be added as message information to a log entry. FIG. 3A-3C illustrates one embodiment of such an addition. Referring to FIG. 3A, the individual uses a user interface tool to take a measurement of an object that appears in an image of a study. In one embodiment, an auto measurement tool is used. In response to the measurement, measurement data appears on display area 102. FIG. 3B illustrates a drop down menu 302 that can be utilized by the user to select a "copy text" function that causes the text from the measurements 301 to automatically appear in the log entry box 113 as measurement data 303 shown in FIG. 3C. Thus, in this way, text or other annotations are made by the user in display area 102 may be included in log entries automatically.

In one embodiment, the log does not only show the log of the current study but also shows the log entries of one or more other studies. For example, in one embodiment, the log may show the entries of all the studies associated with the current patient. This may make it easier to review the history of the patient. This is also advantageous in that other captured display states, snapshots, associated with other studies may be quickly accessed and viewed by an individual. This would make comparison between two studies (e.g., a current study and a previous study) much easier.

In one embodiment, when a user opens one study, the system automatically obtains all the logs associated with the patient and displays all the logs in a single log. Note that if another party viewing one of those logs at another location makes a change to the log they are viewing, the change gets propagated to the study so all viewers of the study get their log updated.

In one embodiment, the user interface provides the means to filter the logs based to include the logs of one or more studies. FIGS. 4A and 4B illustrate a log user interface that includes filter types 400. In one embodiment, the filter types by which logs may be filtered include a type's field, a user's field, a studies field, and a timeline. As shown in FIG. 4A, the studies filter indicates only the current study 401 has been selected. In such a case, only log entries of the current study are shown in the log interface. In FIG. 4B, the studies filter indicates that all studies 402 are to be shown. In such a case, the log interface includes entries of all the logs. In one embodiment, indents are used for identifying who created each log entry. For example, log entries created by one individual are displayed with left-indent while entries created by others are displayed with right-indent.

Figure 4D:
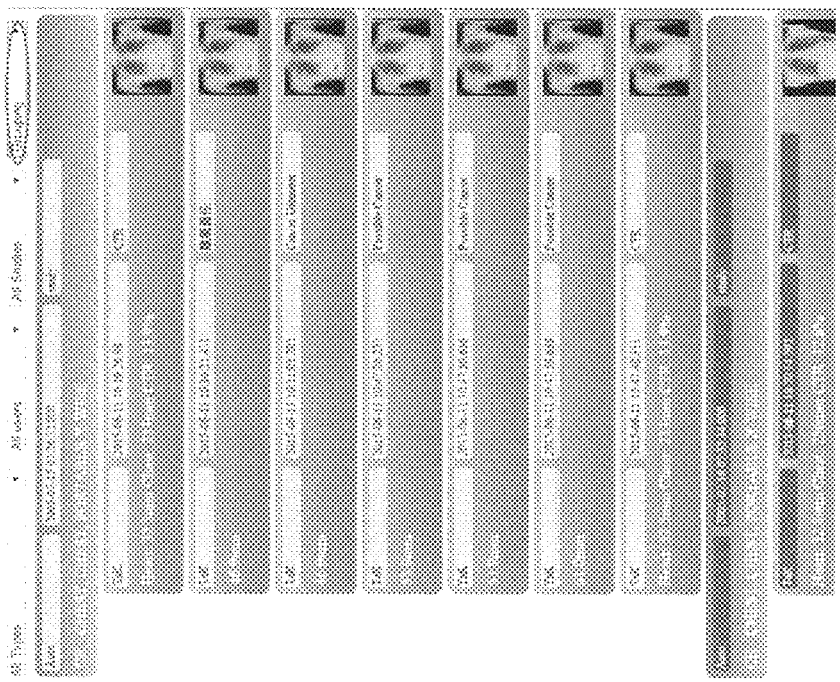
FIG. 4D illustrates log entries ordered according to a grouping.
Figure 4C:
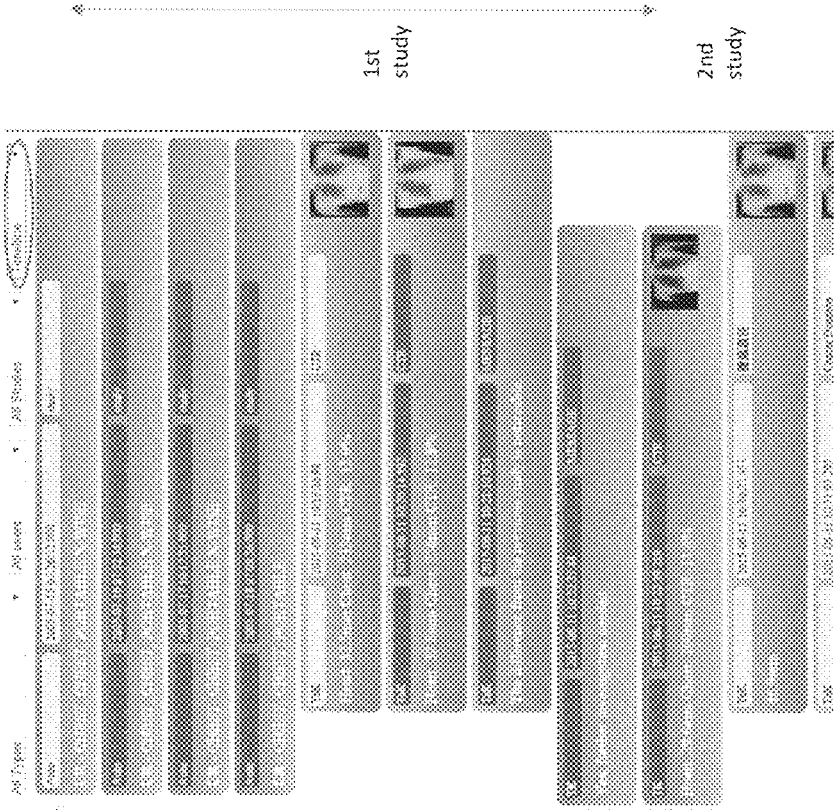
FIG. 4C illustrates log entries grouped by timeline.

Other filters may be used to enable logs to be show logs grouped by study. In one embodiment, the timeline is selected that allows log entries to be ordered by their timestamp. An example of this is shown in FIG. 4C. In another embodiment, the logs can be grouped by study and ordered by their timestamp in each study. This is done by selecting the grouping menu item. An example of this is shown in FIG. 4D.

In one embodiment, the log user interface allows for the assignment of the log type to each log. Assigning types to log entries allows the user to filter the logs by log type. For example, the same type of measurement result (of all studies of the patient) can be shown in order, thereby enabling a user to check for trends of the patient efficiently. FIGS. 5A-C illustrates the log type assignment and filtering logs with different types. Referring to FIG. 5A, input box 303 allows the user to assign different types to the log entries. In one embodiment, the categories are predefined. In another embodiment, the user is able to insert the type and not use a default type. FIGS. 5B and 5C illustrate the filtering logs of different types. In the case of FIG. 5B, the type is CTR, while in FIG. 5C, the type is cancer diameter.

In one embodiment, logs can be added automatically. For example, in one embodiment, when a new study is completed, a new log is added representing the study including the procedure information associated with the procedure recoded in the study. In such a case, by filtering the "study" log type, the study list of the patient can be shown. In another embodiment, when a report is finalized and sent from a dictation system, a new log representing the report is added. In such a case, by filtering the "report" log type, a report list of the patient can be shown. Furthermore, in another embodiment, measurement results are automatically obtained from the server and are added to a log. In this case, the users can rely on or refer to them (or of course do the same measurements by themselves) in response to the automatic addition of the measurement results.

Figure 7:
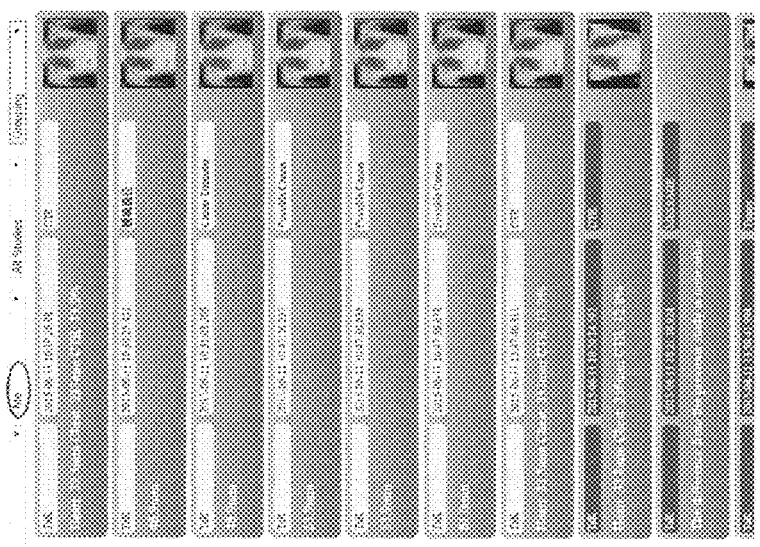
FIG. 7 illustrates a log filtered based on an individual to show logs created by the current user.
Figure 6:
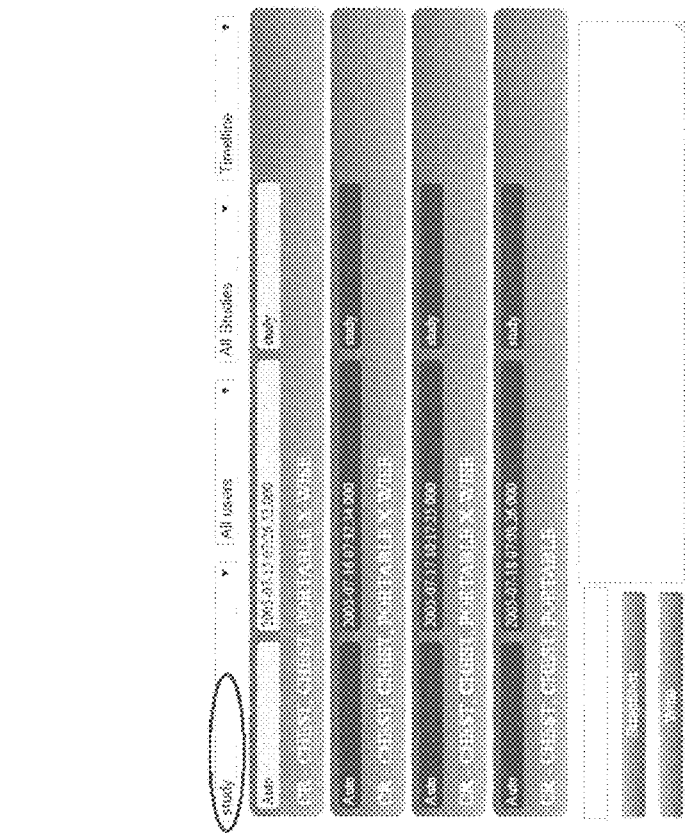
FIG. 6 illustrates an example of filtering for all study log types by choosing log interface entry option.

FIG. 6 illustrates an example of filtering for all study log types by choosing log interface entry option. In another embodiment, logs may be filtered based on user type. For example, all the logs created by a particular individual may be presented in the log interface by specifying the individual. FIG. 7 illustrates a log filtered by "me" to show logs created by the current user.

Other filter types include being able to specify a log type and then only select log entries associated with type to be displayed. Similarly, the user interface containing the log allows the user to select the log entries of "all users" or a subset of users for display.

In one embodiment, when a document associated to a study is uploaded to the server, a new log entry is added to the study. In one embodiment, the document can be uploaded both from display area for the logs and/or from another display area and the document can be opened from the log entry similarly to snapshot.

Figure 8:
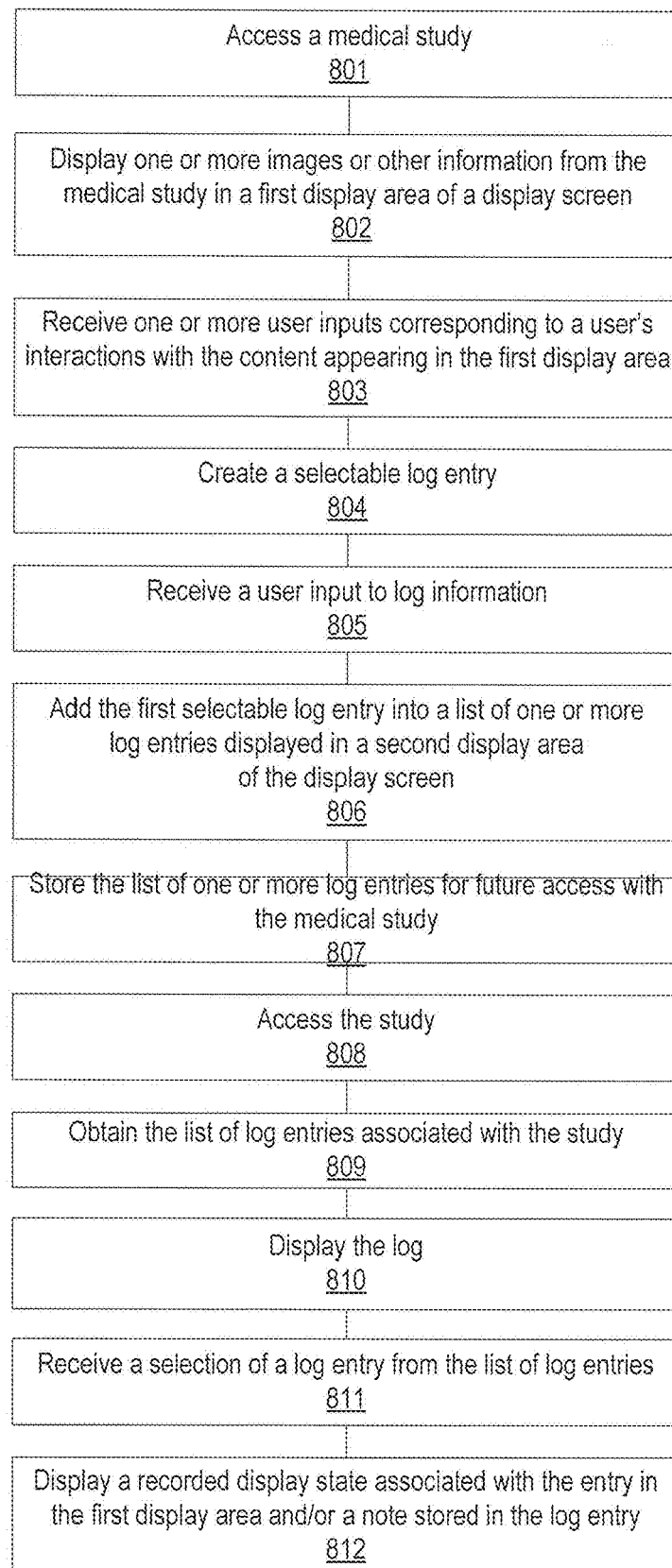
FIG. 8 is a flow diagram of one embodiment of a process for logging information.

FIG. 8 is a flow diagram of one embodiment of a process for logging information. The process may be used to create log entries to support using the log when comparing a study with one or more other studies, requesting assistance from other individuals (e.g., physicians, medical practitioners, etc.), performing collaboration with other individuals, performing the other use cases described herein, etc.

The process is performed by processing logic that may comprise hardware (circuitry, dedicated logic, etc.), software (such as is run on a general purpose computer system or a dedicated machine), firmware, or a combination of two or more of these.

Referring to FIG. 8, the process begins by processing logic accessing a medical study (processing block 801). In one embodiment, the medical study is accessed from a remote storage location (e.g., a server, cloud-based storage system, a PACS, etc.).

Once accessed, processing logic displays one or more images or other information from the medical study in a first display area of a display screen (processing block 802). The display screen may be part of a computing device (e.g., computer system, workstation, etc.). In one embodiment, the first display area comprises one or more windows, which may or may not overlap, partially or otherwise, with each other.

While information from the medical study is displayed in the first display area on the display screen, processing logic receives one or more user inputs corresponding to a user's interactions with the content appearing in the first display area (processing block 803). This is optional and no interaction needs to be performed to subsequently log information. In one embodiment, the processing logic receives inputs from the user to, for example, perform image processing and/or manipulation operations (e.g., panning, zooming, etc.) to the content appearing in the first display area, make additions, deletions or modifications to annotations or other graphical elements appearing in the content in the first display area, to take measurements with respect to objects appearing in the content in the first display area, etc.

Subsequently, processing logic creates a selectable log entry (processing block 804). In one embodiment, creating the selectable log entry includes recording a display state that represents a display layout of a medical information compilation, including display attributes of information, in the first display area, including at least one of a medical image, one or more medical notes, or a medical record and adding a reference pointer to the first selectable entry, where the reference pointer points to a memory location at which the display state is stored. Note that including the captured displayed state is optional and not required for each or any log entry. In one embodiment, creating the selectable log entry includes receiving text or other data (e.g., alphanumeric data) from a user via a user interface (e.g., text entry box) and adding the received information to the selectable log entry. Note that including the received text or other data from a user is optional and not required for each or any log entry.

Then, processing logic receives a user input to log information (processing block 805). In one embodiment, processing logic receives an indication that a user has selected, via a cursor control device, a graphical user interface element (e.g., a button) in a display area associated with the log that causes a log entry to be created and added to the log. Alternatively, a different type of user interface element (e.g., a pull down menu, etc.) may be used to notify the processing logic that a user wants to create a log entry. In one embodiment, the user interface element is located in a different display area than the content from the study is being displayed. For example, the user interface element may be in the same display area as the log is being displayed.

In response to the user input to log information, processing logic adds the first selectable log entry into a list of one or more log entries displayed in a second display area of the display screen (processing block 806).

After a log entry has been created, processing logic stores the list of one or more log entries with the log (processing block 807). In one embodiment, the log is stored separately from the study, but a reference or pointer to the log is included in the study. In one embodiment, after the study has been closed and is no longer being reviewed, the log is stored.

Subsequently, processing logic access the study (processing block 808), obtains the list of log entries associated with the study (processing block 809), and displays the log (processing block 810).

Once the logic is display, processing logic receives a selection of a log entry from the list of log entries (processing block 811) and displays a recorded display state associated with the entry in the first display area and/or a note stored in the log entry (processing block 812).

Figure 9:
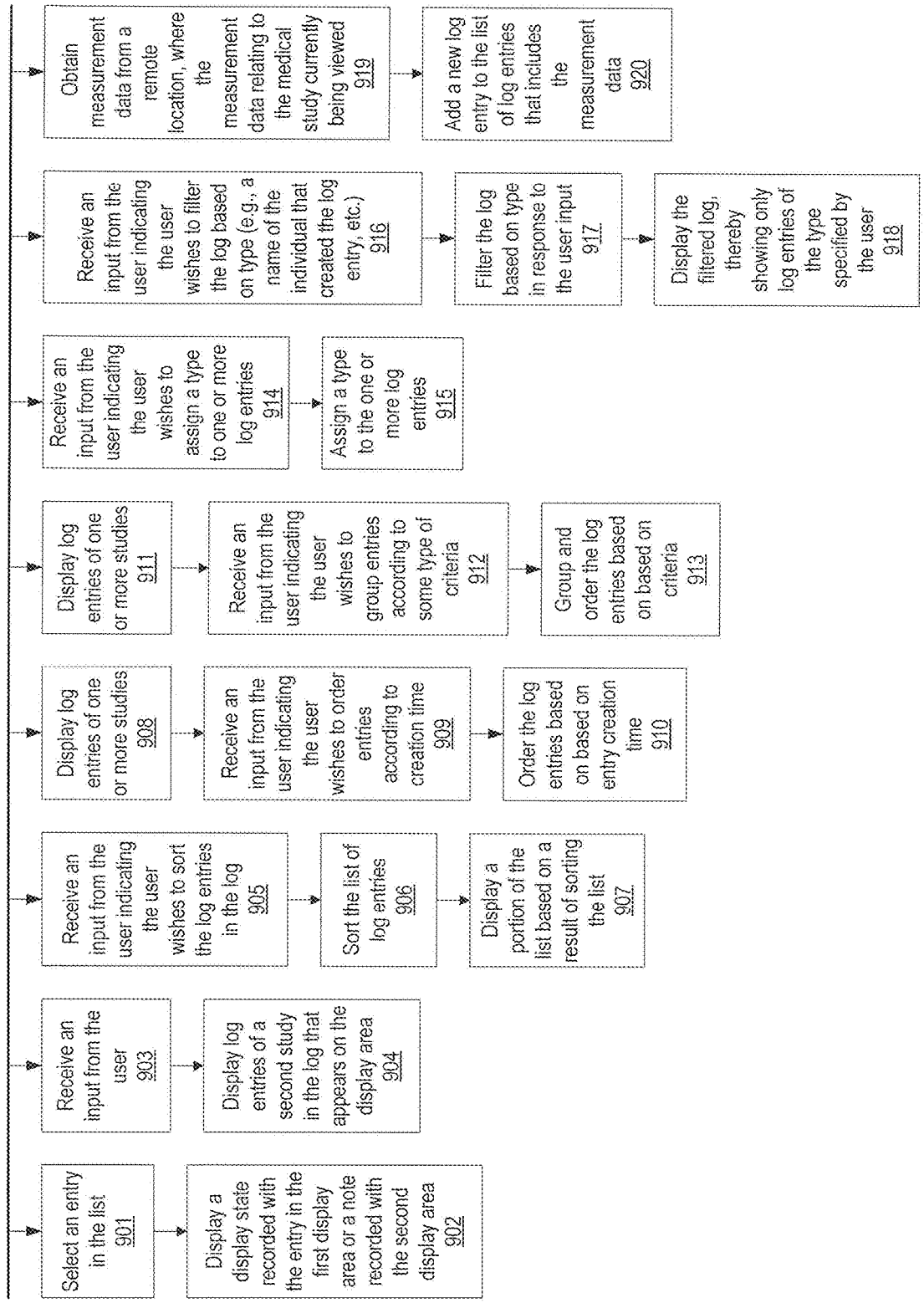
FIG. 9 illustrates various process that may be performed with logs.

After at least one log entry has been added to a log, the log includes one or more log entries and as describe above, the user may perform a number of actions while interacting with the log and its log entries. FIG. 9 is a flow diagram of one embodiment of a process for interacting with a log. The process is performed by processing logic that may comprise hardware (circuitry, dedicated logic, etc.), software (such as is run on a general purpose computer system or a dedicated machine), firmware, or a combination of two or more of these.

The process includes a number of optional flows that may occur based on which user inputs are received. Referring to FIG. 9, in one embodiment, in response to receiving a user input specifying a specific log entry (e.g., receiving a cursor control device input from a user clicking on a log entry, etc.), processing logic selects an entry in the list (processing bock 901) and displays a display state recorded with the entry in the first display area or a note recorded with the second display area (processing block 902). When one selects a log entry, while the snapshot appears on the display screen, any text (memo) in the log entry appear in the log display area.

In one embodiment, processing logic receives an input from the user (processing block 903) and displays log entries of a second study in the log that appears on the display area (processing block 904).

In one embodiment, processing logic receives an input from the user indicating the user wishes to sort the log entries in the log (processing block 905), sorts the list of log entries (processing block 906), and displays a portion of the list based on a result of sorting the list (processing block 907).

In one embodiment, processing logic displays log entries of one or more studies (processing block 908), receives an input from the user indicating the user wishes to order entries according to creation time (processing block 909), and orders the log entries based on based on entry creation time (processing block 910).

In one embodiment, processing logic displays log entries of one or more studies (processing block 911), receives an input from the user indicating the user wishes to group entries according to some type of criteria (e.g., by study) (processing block 912), and groups and orders the log entries based on based on criteria (processing block 913).

In one embodiment, processing logic receives an input from the user indicating the user wishes to assign a type to log entries (processing block 914) and assigns a type to one or more log entries (processing block 915). In one embodiment, a different type can be assigned to individual log entries.

In one embodiment, processing logic receives an input from the user indicating the user wishes to filter the log based on type (e.g., a name of the individual that created the log entry, a type of log entry, a study associated to entries (current study or all studies), etc.) (processing block 916), filters the log based on type in response to the user input (processing block 917), and displays the filtered log, thereby showing only log entries of the type specified by the user (processing block 918).

In one embodiment, processing logic automatically obtains measurement data from a remote location, where the measurement data relating to the medical study currently being viewed (processing block 919) and adds a new log entry to the list of log entries that includes the measurement data (processing block 920).

Various Use Cases for the Log

There are a number of use cases that illustrate use logging in specific situations. These include, for example, the comparison of studies, report generation, conferences, and collaboration between users.

In one embodiment, the log may be used in the comparison of studies, such as comparing an old study and a new study in the same subject matter (e.g., mammography studies of a patient taken at two different times). In such a case, a physician may want to review a previous study to see what their thinking process was at the time of the time of the review of the older study. In such a case, the physician can review the log associated with the older study, including performing a review of notes and/or memos along with any snapshots of captured display states to determine what the thinking was with respect to the subject of the study in the past.

When comparing studies, if a log entry is made, only the log of the current study is updated with the new log entry. In another embodiment, a user is show content from two or more studies on one display area and the display state is captured as a snapshot, thereby capturing content of the multiple studies, and entry into the log associated with each study is made. In another embodiment, only the log of the main study, not those used for comparison purposes, is modified to include the new log entry. In yet another embodiment, if another study is open while the user reviews a first study with the log and the additional study has a log associated with it, one or more portions of the log may be added and included into the log of the current study.

In another embodiment, the log is used in the creating of a report. In one embodiment, an entire thread of the log is included in a report. In another embodiment, the only portions of the log (e.g., one or more particular entries) are included in the report. For example, in one embodiment, the reporting tool has a template thread that includes graphical user interface features that enable entries of the log to be added to the report. The additions may include any captured display states, which are then added to the report. In such a case, a simple graphical user interface feature can be used to add log entries or other content to the report.

The log may be used to facilitate conferences between physicians. For example, a physician reviewing the study may make notes and capture display states are snapshots. The notes may prompt a subsequent viewer of the log to review specific items that the previous user had identified. For example, a number of one or more entries a physician reviewing the study may create one or more entries and include notes such as, for example, "look at this" or "note the abnormalities". Snapshots may be captured and included in the log entries such that another physician subsequently reviews the log they are prompted to review specific items that appear in the captured display states.

In another embodiment, the log may be used to collaborate between individuals, such as, for example, for physicians, etc. these individuals may be at different locations. For example, a pair of individuals, for example, physicians can review studies at different times and provide feedback in the form of notes and memos and include one or more snapshots that display their findings and that will present their ideas and/or findings to a subsequently reviewing individual. More specifically, when reading the study of a first patient, a doctor may need help from another doctor. In such a case, the first doctor creates a log with a captured display state and posts a request for help to the other individual doctor or a group that includes that doctor. Subsequently, that doctor receives the request for help and subsequently finds time provide an answer to the log, which they post by creating a log entry with their response and may or may not include a new snapshot. The fact that the log has been updated is posted back to the first physician. The first physician notices that the requested physician has provided an answer. At a convenient time, the first physician can access the log and read the answer from the other doctor in the log. Such a process is very helpful and allows the two physicians to exchange ideas in a collaborative manner while not having to interrupt the other doctor.

Note that in such a case, the application may include a notification feature that allows one party to notify the other that there is a request for help or that the other party to review some material in the study. There are many ways to provide such a notification. For example, if the two users are using the same application, a notification feature of that application may allow a user to simply select an individual's name using some user interface element (e.g., a drop down menu) which causes a notification to appear on the other person's display screen. In one embodiment, in such a case, the user being requested to review the study can click on the notification and the study may appear on their display screen. In one embodiment, only the relevant portions of the study in the log are displayed on the display screen.

Figure 10:
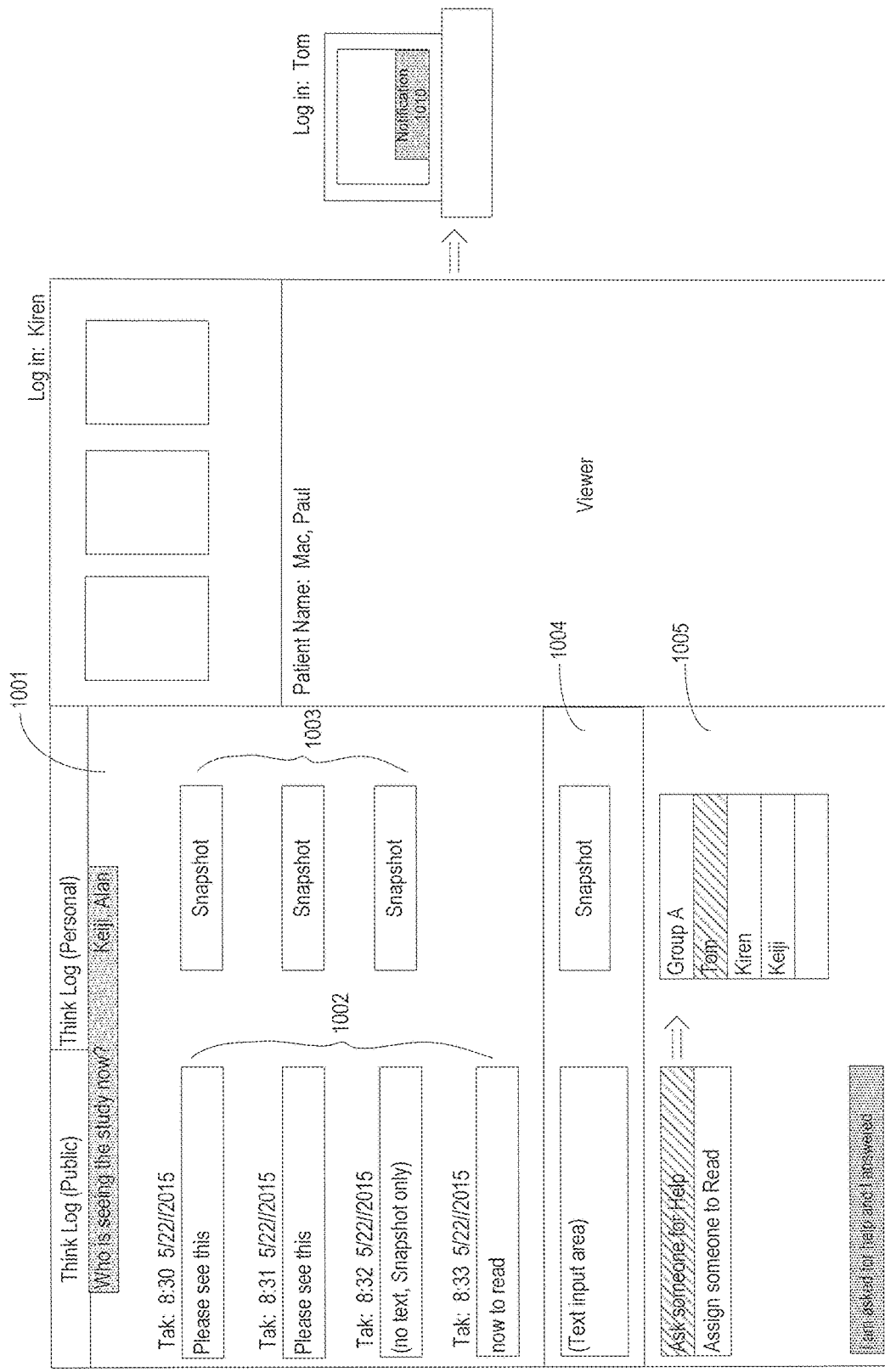
FIG. 10 illustrates an example of collaboration.

FIG. 10 illustrates an example of collaboration. Referring to FIG. 10, display screen 1001 includes a number of log entries 1002, many of which include snapshots 1003. Display area 1001 also includes a box 1004 to allow adding new log entries and an area with a drop down menu to assign a party to read a study or ask a party for help and a drop down menu to select an individual(s) or group for the request. When assigned, notification 1010 is sent to the assigned individual or group. Other notifications may be used. For example, when a party is asked to review a study by an individual, in one embodiment, the individual receives a notification when the party opens the study, a question the individual asked has been answered, a review of the study has be completed, or a new log entry has been added to the log.

Figure 11:
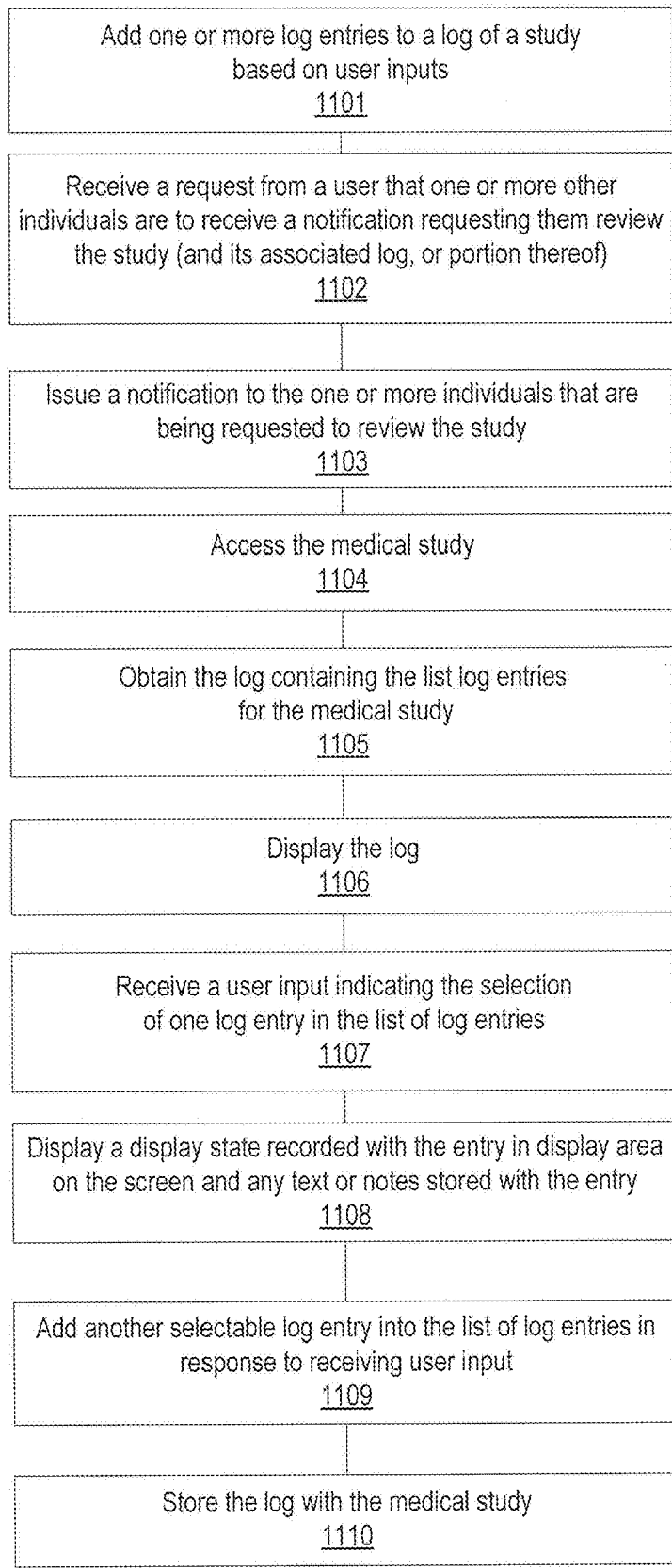
FIG. 11 is a flow diagram of one embodiment of a process for using a log for collaboration.

FIG. 11 is a flow diagram of one embodiment of a process for using a log for collaboration. The process is performed by processing logic that may comprise hardware (circuitry, dedicated logic, etc.), software (such as is run on a general purpose computer system or a dedicated machine), firmware, or a combination of two or more of these.

Referring to FIG. 11, the process begins by processing logic adding one or more log entries to a log of a study based on user inputs (processing block 1101). In one embodiment, the process described above with respect to FIG. 8 is used to add log entries.

After adding one or more log entries, processing logic receives a request from a user that one or more other individuals are to receive a notification requesting them review the study (and its associated log, or portion thereof) (processing block 1102). This indication may be an assignment by one physician to one or more other physicians that are collaborating on a patient.

In response to the request, processing logic issues a notification to the one or more individuals that are being requested to review the study (processing block 1103). In the case where the other individuals reviewing the study use the same application as the requesting individual, the application may provide a notification on a user interface (e.g., a dashboard) that is generated by the application. In another embodiment, the notification is made by sending a message (e.g., email, text message, etc.) to the individuals.

Subsequent to the notification being issued and being received by the individual(s), processing logic accessing the medical study (processing block 1104), obtains the log containing the list log entries for the medical study (processing block 1105) and displays the log (processing block 1106). The access to the medical study occurs in response to one of the individuals requesting access to the study. This request may occur by clicking on the name of the study appearing, for example, in a worklist, or an icon representing the study in a user interface.

Thereafter, processing logic receives a user input indicating the selection of one log entry in the list of log entries (processing block 1107) and, in response thereto, displays a display state recorded with the entry in display area on the screen and any text or notes stored with the entry (processing block 1108). The text or notes may be displayed in the same display area that displays the log; however, this is not required.

Processing logic may also add another selectable log entry into the list of log entries in response to receiving user input (processing block 1109) and thereafter stores the log with the medical study (processing block 1110).

Overview of Snapshot

Figure 12:
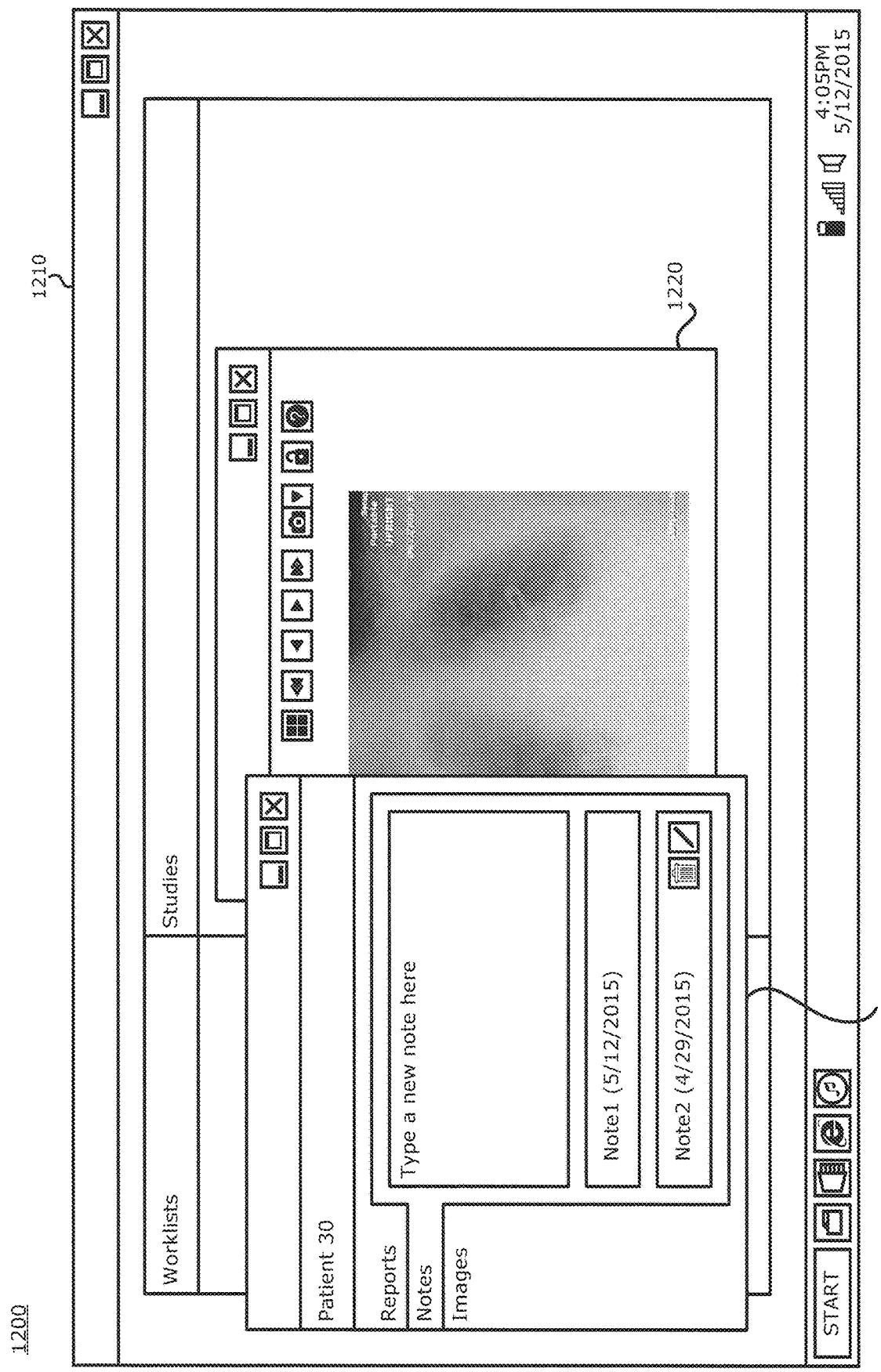
FIG. 12 is a first exemplary embodiment of a plurality of user interactive display screens.

Referring to FIG. 12, a first exemplary embodiment of a plurality of user interactive display screens is shown. The display 1200 includes a plurality of display screens 1210, 1220 and 1230. FIG. 12 illustrates one embodiment of how a user (e.g., a doctor, a medical technician or a nurse) simultaneously views a plurality of medical images and notes relevant to one or more of the medical images or of the subject of one or more of the medical images. The display screen 1210 shows a home screen comprising a listing of one or more worklists, one or more collections and one or more studies. The display screen 1220 shows a medical image, specifically an x-ray of a chest. Finally, the display screen 1230 illustrates a text box for adding notes pertaining to the patient (e.g., "Patient 30") or reviewing previously recording notes.

After reviewing at least the display screens 1220 and 1230, a user may exit the viewing application (e.g., to take a break, examine another patient, etc.) but may wish to return to the viewing state just prior to exiting the viewing application, or to a particular state of interest. Without implementing the snapshot feature as discussed in this disclosure, the user would be required to open multiple display screens (e.g., the display screens 1220 and 1230) and adjust the medical image of the display screen 1220, if applicable. The user may not be able to recall the steps required to obtain the viewing state just prior to previously exiting, or to obtain the particular state of interest. Therefore, creating a layout with the desired medical images and/or notes and having a snapshot generated would allow the user to quickly recall the state just prior to previously exiting, or recall the particular state of interest.

Generation of a Snapshot

Figure 13:
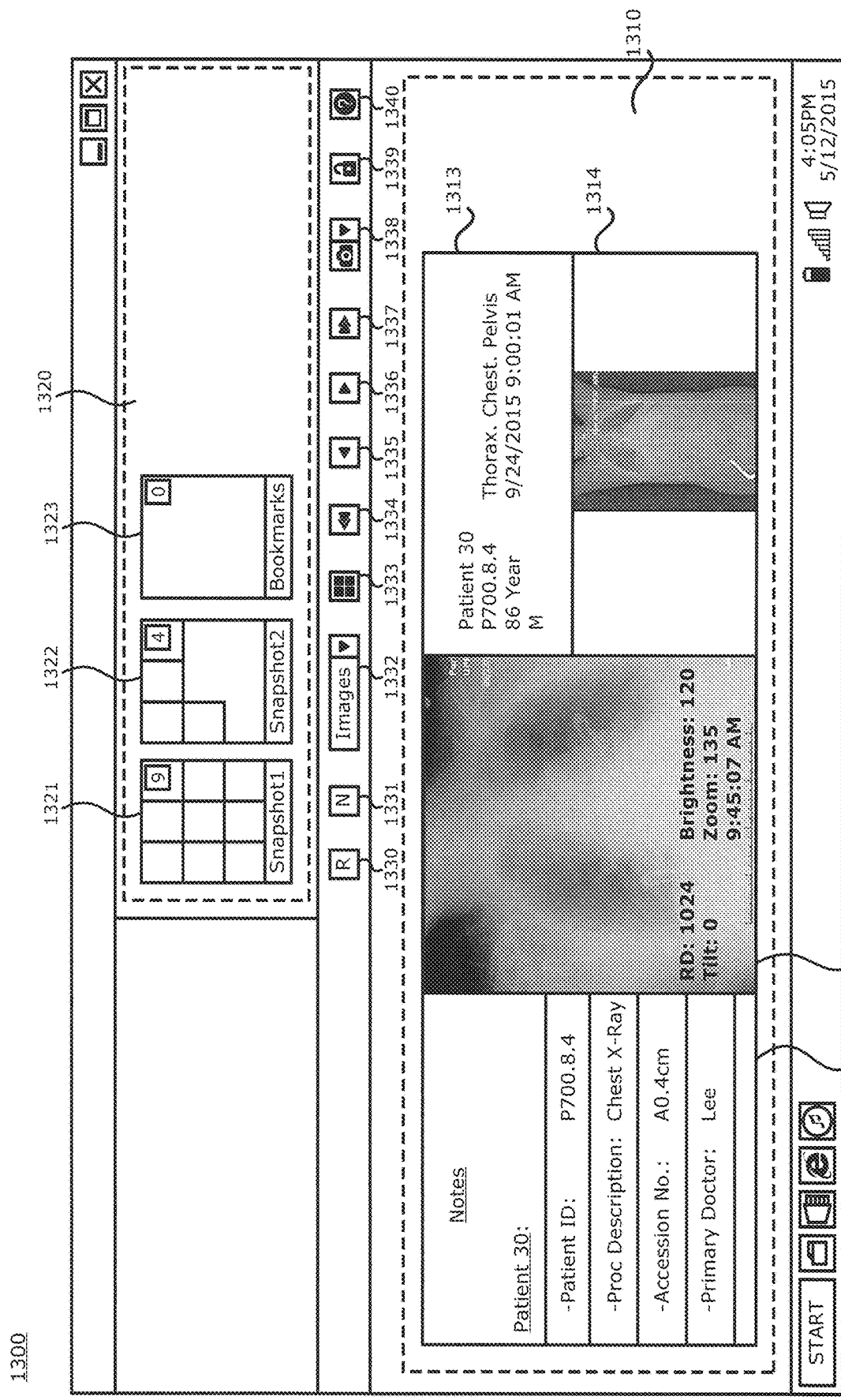
FIG. 13 is an exemplary embodiment of a display screen that illustrates a plurality of display areas, each containing information pertaining to a particular patient.

Referring now to FIG. 13, an exemplary embodiment of a display screen that illustrates a plurality of display areas, each containing information pertaining to a particular patient is shown. Herein, rendered by display control logic, discussed below, the display screen 1300 includes a user interactive display screen 1310, a history display area 1320 and a plurality of icons 1330-1340 indicating a plurality of actions that may be taken by the viewer. In this embodiment, the user interactive display screen 1310 includes four display areas: a notes display area 1311, a first medical image 1312, a report display area 1313 and a second medical image 1314. The four display areas 1311-1314 are set forth in a predefined layout selected by a user. As will be discussed below in accordance with FIG. 14, other layouts may exist other than the layout illustrated in the user interactive display screen 1310.

As is seen in the user interactive display screen 1310 of FIG. 13, a notes display area 1311 may include information relevant to a particular patient, e.g., "Patient 30." The notes display area 1311 includes a plurality of examples of patient information that may be included in the notes display area 1311 but in other embodiments, more or less information may be included therein. The medical image 1312 illustrates one example of a medical image that may be included in a user interactive display screen. The medical image 1312 illustrates a first x-ray. As is seen, the medical image 1312 may include markings to identify characteristics of the state in which the x-ray was taken (e.g., a brightness level, a zoom level and/or a time). Alternatively, the markings may be used to refer to the adjustment of the medical image 1312 once the medical image 1312 is placed in a display area of the layout.

The record display area 1313 may include information of the subject of the medical images 1312 and 1314. In the embodiment of FIG. 13, the record display area 1313 includes information of the Patient 30, in accordance with the notes display area 1311, to provide the viewer one or more pieces of information regarding the subject's age, sex, areas of prior medical issues, etc. As one skilled in the art would recognize, other medical attributes may be provided in the records display areas 1313 than just those illustrated herein. The medical image 1314 may provide a second perspective of the subject of the medical image 1312. In one embodiment, the medical image 1312 may illustrate an x-ray focused on the patient's chest in order to determine whether a lung has been punctured or a rib has been fractured. The medical image 1314 may offer the viewer a second perspective of the patient, illustrating an object piercing the patient's body.

In other embodiments, any combination of medical images may be placed within one or more display areas of the layout. For example, a plurality of medical images of a single patient may be placed side by side, similar to the embodiment portrayed as user interactive display screen 1310. Alternatively, one or more medical images of a patient's progression from an initial medical image of an injury to a healed state including several medical images taken periodically during recovery. This progression may enable doctors to adequately monitor a patient's recovery. Alternatively, a doctor may want to compare a plurality of medical images of a similar perspective of multiple patients.

The history display area 1320 of the display screen 1300 may include one or more snapshots that have previously been viewed. For example, the snapshot 1321 and the snapshot 1322 are illustrative examples of snapshots that may have been viewed previously. Additionally, an icon placed on the snapshot 1321 or 1322 may be used to indicate the number of states included within the snapshot 1321 or 1322. In the embodiment of FIG. 13, a numerical icon placed on the snapshot 1321 indicates there are nine states within the snapshot 1321, similarly an icon indicates there are four states within the snapshot 1322. The history display area 1300 may also include a "Bookmarks" option 1323. The bookmarks option 1323 may store links to snapshots, or particular states thereof, for quick access.

The display screen 1300 may also include a plurality of icons that a viewer may utilize to invoke various functionalities. In the embodiment illustrated in FIG. 13, the icon 1330 may represent access to a records database so that a patient's records may be imported into the layout. The icon 1331 may represent access to a notes database so that a previously taken note may be imported into the layout. The icon 1331 may also include the functionality of enabling the viewer (e.g., creator of the layout or viewer) to import a new note into the layout. The icon 1332 may represent access to an images database enabling a viewer to import one or more medical images into the layout. The icon 1333 may represent access to a database storing one or more templates of layouts. In some embodiments, a viewer may select an initial layout template, or change layout templates through the icon 1333. The icons 1334-1337 may enable a viewer to step through steps taken to adjust a medical image. For example, assuming the medical image 1312 is selected, the icon 1334 may enable the viewer to return to the initial, unadjusted state of medical image 1334; the icon 1335 may enable the viewer to return to one step prior to the current adjusted state (e.g., return to the previous zoom level, or decrease the brightness level); the icon 1336 may enable the viewer step forward to a next step in the adjusted step; and the icon 1337 may enable the viewer to return to final adjusted state when the snapshot was saved (in such an embodiment, it is assumed that in order to use the icons 1336-1337, one or more of the icons 1334-1335 were previously used by the viewer).

The icon 1338 may represent access to one or more snapshot features such as saving the state of the layout (e.g., generating a snapshot), naming the snapshot (the particular state) and/or assigning the snapshot (or particular state) to a specified collection. The icon 1339 may enable the creator, or viewer, to lock the user interactive display screen 1310 such that no adjustments can be made to one or more display areas of the current saved state unless the user interactive display screen 1310 is unlocked (e.g., via a password). The icon 1340 may represent access to a help guide or a settings menu.

The state in which the user interactive display screen 1310 is opened may be a configurable setting. For example, a user may configure the display control logic, (discussed below), to render the medical compilation (e.g., the study) at a predefined state when the medical compilation is selected. In one embodiment, the latest saved state may be automatically rendered when the medical compilation is selected. In a second embodiment, the first saved state may be automatically rendered when the medical compilation is selected.

Figure 14:
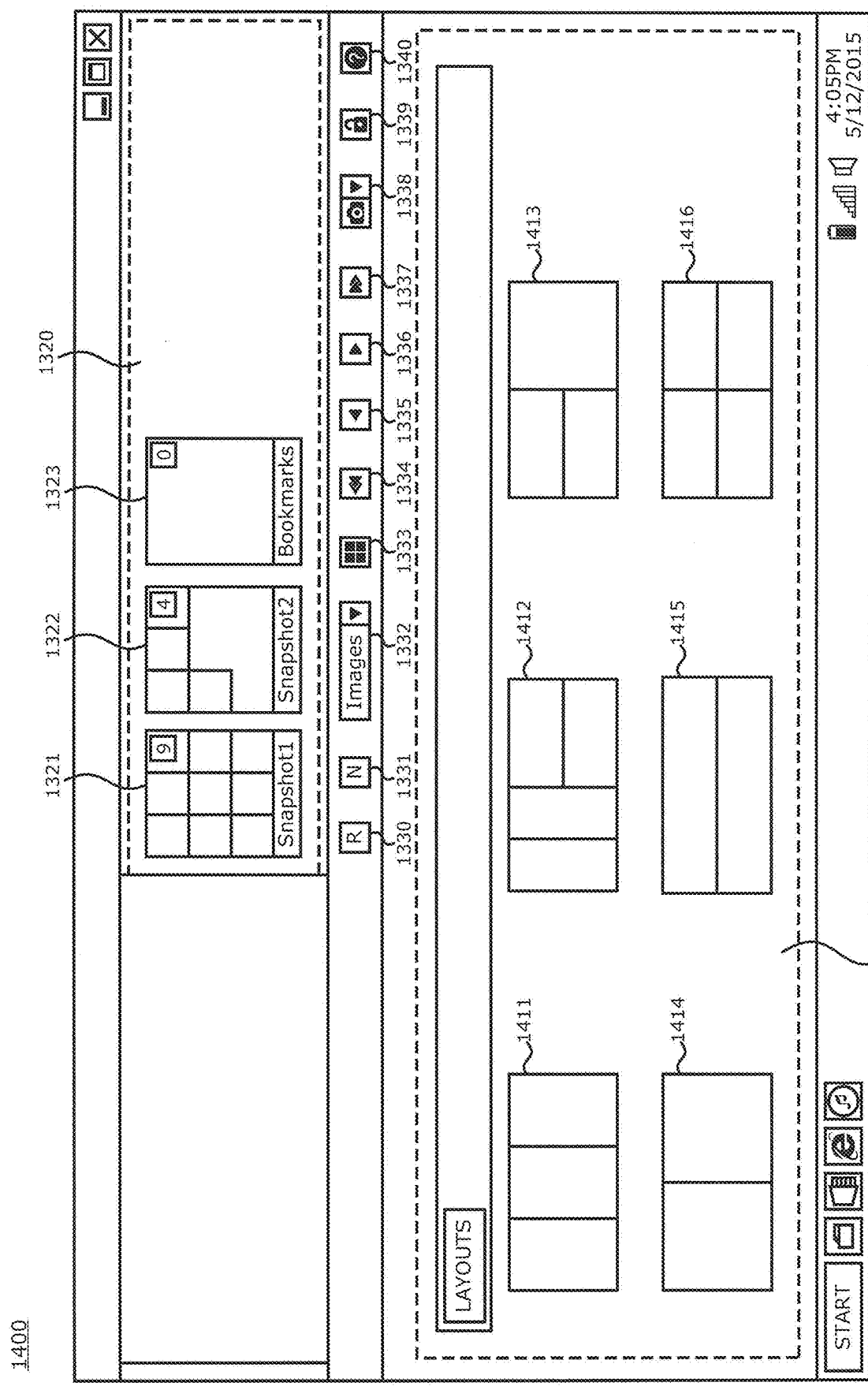
FIG. 14 is an exemplary display layout template selection screen that lists potential display layout templates that are selectable by a user for snapshot generation.

Referring to FIG. 14, an exemplary layout template selection screen that lists potential layout templates that are selectable by a user for user interactive display screen generation is shown. The display screen 1400 includes at least the history display area 1320 and the icons 1330-1340 as discussed in FIG. 13. Additionally, the display screen 1400 includes a layout templates display screen 1410 that includes one or more layout templates that a user may select while creating a layout, which is in turn saved as a snapshot (or state thereof).

For example, the layout templates display screen 1410 includes layout templates 1411-1416. Each of the layout templates 1411-1416 includes a varied layout for one or more medical images, notes, records, or other information or data that may be relevant to a doctor's examination or review. In one embodiment, a user may have obtained a first piece of data (e.g., a first medical image) that the doctor wishes to compare with a second medical image that will be taken in the near future as well as notes regarding both medical images. The doctor may select a layout template, for example the layout template 1416, in order to import the first medical image and notes pertaining to the first medical image. Subsequently, when the second medical image is obtained, the doctor may import the second medical image into the layout template 1416 as well as notes pertaining to the second medical image. Therefore, selection of a layout template 1411-1416 allows a doctor, nurse and/or medical technician to easily place medical data into a layout that promotes ease of viewing, and that can be saved as a snapshot or a state thereof for future reference.

Additionally, display control logic, discussed below, may include logic for generating templates based on a user creating one or more templates. In one embodiment, a user may alter a layout template to include one or more additional display areas, or remove one or more display areas. For example, a user may select the layout template 1411 and upon attempting to import a fourth piece of medical data, the control display logic may import the fourth piece of medical data into a fourth display area, splitting one display area into two, or condensing the current display areas and adding a fourth display area. Upon altering a layout template, the display control logic may add the newly created layout to the layout templates of display area 1410. In another embodiment, the user may be prompted as to whether the altered layout is to be added to the layout templates of the display area 1410.

Accessing Snapshots from a Home Screen

Figure 15:
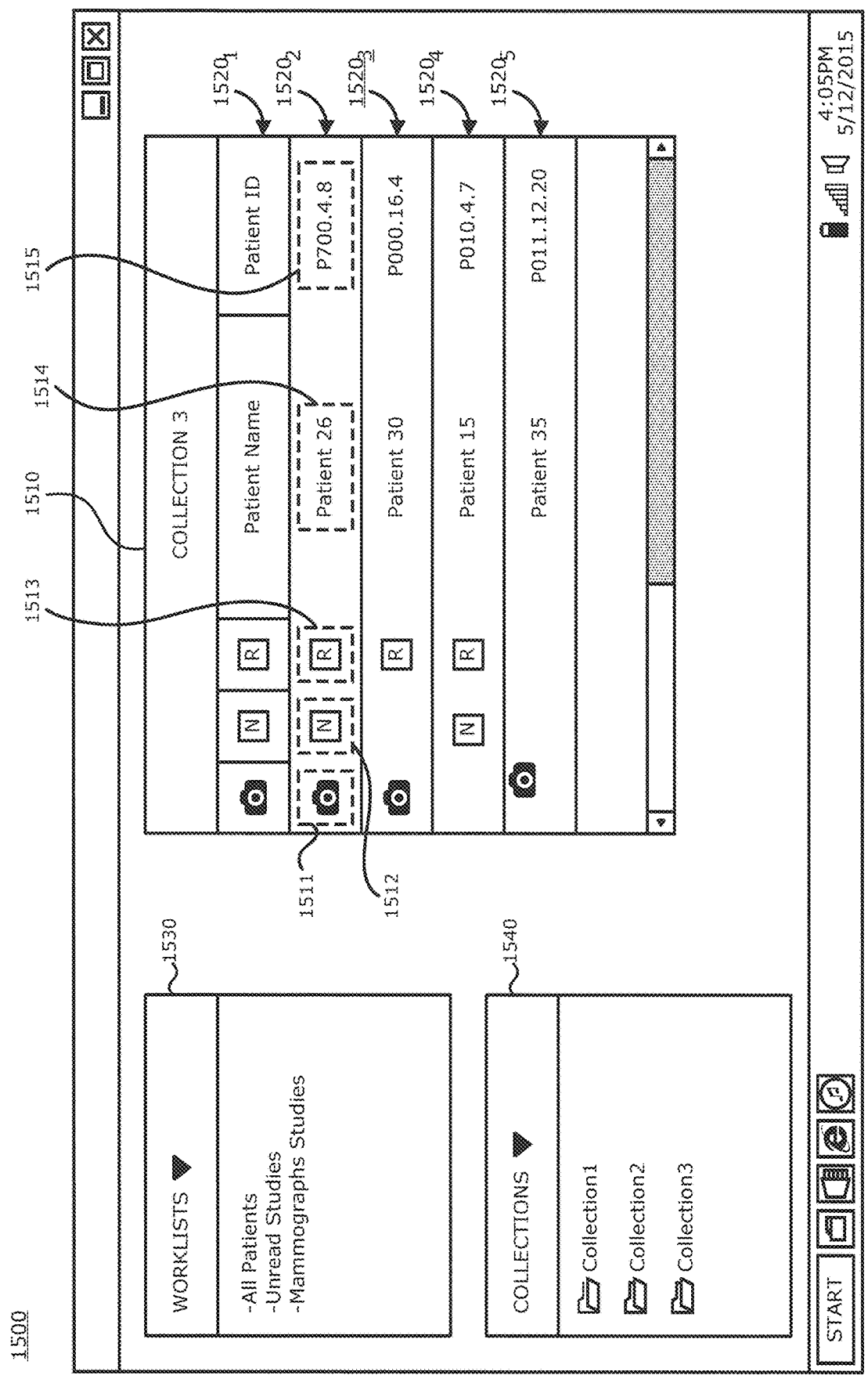
FIG. 15 is an exemplary display screen that illustrates a worklists display area, a collections display area and a listing of studies within a collection.

Referring to FIG. 15, an exemplary display screen that illustrates a worklists display area, a collections display area and a listing of studies within a collection is shown. In one embodiment, the display screen 1500 may represent a "home" screen providing access to a plurality of studies, worklists, collections and/or or individual snapshots, or states thereof. Herein, the display screen 1500 includes a display area 1510, a worklists display area 1530 and a collections display area 1540.

The worklists display area 1530 and the collections display area 1540 recite worklists and collections, respectively. The term "worklist" refers to a rule-based grouping of studies while the term "collection" refers to a grouping of studies manually assembled by a user. The embodiment in FIG. 15 illustrates three current worklists, "All Patients," "Unread Studies," and "Mammographs Studies." Therefore, for example, all studies (e.g., snapshots, medical images, notes, etc.) that have not been opened may be automatically placed in the worklist titled, "Unread Studies," based one or more rules. Additionally, for example, the worklist titled, "Unread Studies," may also include studies that have not been finalized. With a worklist, a viewer or user is not required to manually add data (e.g., a snapshot, a state of a snapshot, a medical image, etc.) to a worklist grouping, instead, logic, stored on a non-transitory computer-readable medium of an electronic apparatus will automatically add the data to the appropriate worklist Examples, of the electronic apparatus may include a desktop computer, a tablet, a laptop, a "smart" mobile phone, or a dedicated server. Similarly, the logic may remove a study from a worklist according to one or more rules (e.g., a study will be removed from the worklist "Unread Studies" when the study is opened, assuming a rule of the worklist, "Unread Studies," is to place all unopened, e.g., unread, studies into the worklist).

In contrast, studies are added to, or removed from, a collection only when done so manually by a user or viewer. It is envisioned that a combination of a worklist and collection grouping may be implemented wherein a user may manually add to, or remove from, the grouping but also establish rules for automatic addition and removal. Although FIG. 15 illustrates only three worklists and three collections, more or less worklists and/or collections may be provided or created.

As is seen FIG. 15, the studies of "Collection 3" are listed in the display area 1510, wherein the exemplary rows 15201-15205 are illustrated. The row 15201 includes headers for each column of the rows 15202-15205. For example, the row 15202 may include icons in one or more columns including the icon 1511 indicating the presence of a snapshot for the corresponding study of row 15202, the icon 1512 indicating the presence of notes (e.g., by a nurse or doctor) for the corresponding study of row 15202, the icon 1513 indicating the presence of a medical record corresponding to the study of row 15202. Additionally, a patient name 1514 and a patient identification (ID) 1515 corresponding to the study of row 15202 may be included. Furthermore, more or less columns and/or rows may be present in the display area 1510 than are illustrated in FIG. 15. In one embodiment, the icon 1511 may include an icon indicating a number of states available in the snapshot (e.g., as was discussed with the snapshots 1321 and 1322 in the history display area 1320 of FIG. 13).

An Exemplary System

Figure 16:
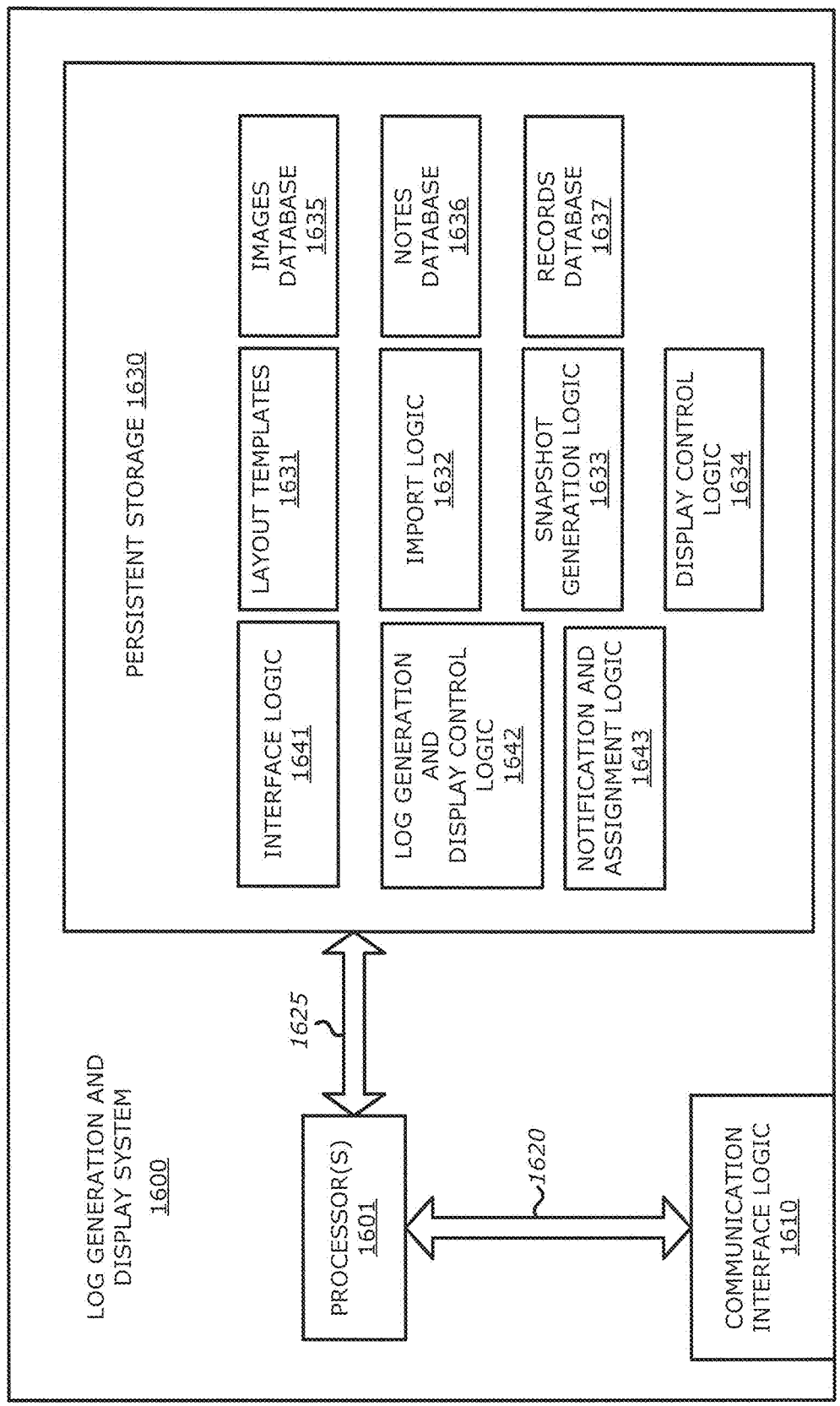
FIG. 16 is an exemplary embodiment of a logical representation of a snapshot generation and display system that generates and renders the displays of FIGS. 13-15.

Referring now to FIG. 16 illustrates an exemplary embodiment of a logical representation of a log generation and display system 1600 that generates and renders the logs discussed above. The system generates individual log entries that can have snapshots such as, for example, shown in FIGS. 13-15. The log generation and display system 1600 includes one or more processors 1601 that are coupled to communication interface logic 1610 via a first transmission medium 1620. The communication interface logic 1610 enables communications with other electronic devices, specifically enabling communication with remote users such as doctors, nurses and/or medical technicians. According to one embodiment of the disclosure, communication interface logic 1610 may be implemented as a physical interface including one or more ports for wired connectors. Additionally, or in the alternative, communication interface logic 1610 may be implemented with one or more radio units for supporting wireless communications with other electronic devices.

The processor(s) 1601 is further coupled to persistent storage 1630 via transmission medium 1625. According to one embodiment of the disclosure, persistent storage 1630 may include (a) user interface logic 1641, (b) log generation and display control logic 1642, (c) notification and assignment logic 1643, (d) the layout templates 1631, (e) an import logic 1632, (f) a snapshot generation logic 1633, (g) a display control logic 1634, (h) an images database 1635, (i) a notes database 1636 and (j) a records database 1637.

The user interface logic 1641 may include logic for enabling interaction between a user and the display areas being displayed on the screen.

The log generation and display control logic 1642 includes logic for controlling the generation of a log, including generating log entries and storing a log with a study, as well as control logic to handle interaction with a log such as, for example, sorting log entries, searching log entries, assigning types to log entries, determining which log entries are to be displayed.

The notification and assignment logic 1643 includes logic to issue and send notifications and/or assignments for study (and log) reviews.

The import logic 1632 may include logic for retrieving one or more pieces of information from a storage device and importing each of the one or more pieces of information into a separate display area of a layout template. For example, the pieces of information may include, but are not limited or restricted to, (i) medical images, including x-rays, mammograms, computerized tomography (CT) scans, magnetic resonance imaging (MRI), positron emission tomography (PET) scan and/or ultrasound imaging, (ii) physician's notes regarding one or more of the medical images and/or (iii) medical records corresponding to one or more of the subjects of the one or more medical images.

The snapshot generation logic 1633 may include logic for saving at least a first state of the layout template. Saving the first state may include storing, at least, (i) the one or more pieces of information, and (ii) viewing properties of each of the one or more pieces of information in a non-transitory computer-readable medium. The display control logic 1634 may include logic for retrieving one of a set of saved states of the layout template for display according to a selection of a user and displaying (e.g., rendering a display screen) the retrieved one of the set of saved states of the layout template. Additionally, the display control logic 1634 may include logic for adjusting one or more of the viewing properties according to instructions by the user (e.g., altering a brightness level, a zoom level, a contrast level, etc.). Furthermore, the display control logic 1634 may include logic for stepping back in a series of adjustments made to one or more pieces of information included in a snapshot (or state thereof). In one embodiment, the display control logic 1634 may, according to instructions received via the user selecting various icons on the display screen, step back to previous states based on adjustments to one or more viewing properties.

For example, assume a doctor had increased the brightness level from 100% to 150% and then increased the zoom level from to focus on a particular aspect of the medical image before saving the state of the layout as a first state of a snapshot and closed the display screen. Upon opening the first state of the snapshot, the doctor (or another user) would see the medical image at a brightness level of 150% and at the increased zoom level focusing on the particular aspect of the medical image. The doctor may then step back to previous states based on the adjustments to the medical image that were previously made. Therefore, the doctor may step back to a normal zoom level and subsequently step back to a brightness level of 100% (e.g., by selecting icon 1335 of FIG. 13, for example). Additionally, the doctor may be able to return to the initial state of the medical image (e.g., by selecting icon 1334 of FIG. 13, for example), step forward, assuming a step back has been taken (e.g., by selecting icon 1336 of FIG. 13, for example) and/or step forward to the state when the first state was saved (e.g., by selecting icon 1337 of FIG. 13, for example). Of course, when implemented as hardware, one or more of these logic units could be implemented separately from each other.

The images database 1635, the notes database 1636 and the records database 1637 may comprise a single non-transitory computer-readable medium storage device or may each be a separate non-transitory computer-readable medium storage device. In one embodiment, each of the databases 1635-1637 may take the form of a hash table on a single non-transitory computer-readable medium storage device. The images database 1635 stores medical images that a user may import into a display area of a layout template. The notes database 1636 stores notes recorded by a doctor, nurse, medical technician, etc., that a user may import into a display area of a layout template. Finally, the records database 1637 stores medical records that a user may import into a display area of a layout template.

An Example of a Snapshot Generation Process

Figure 17:
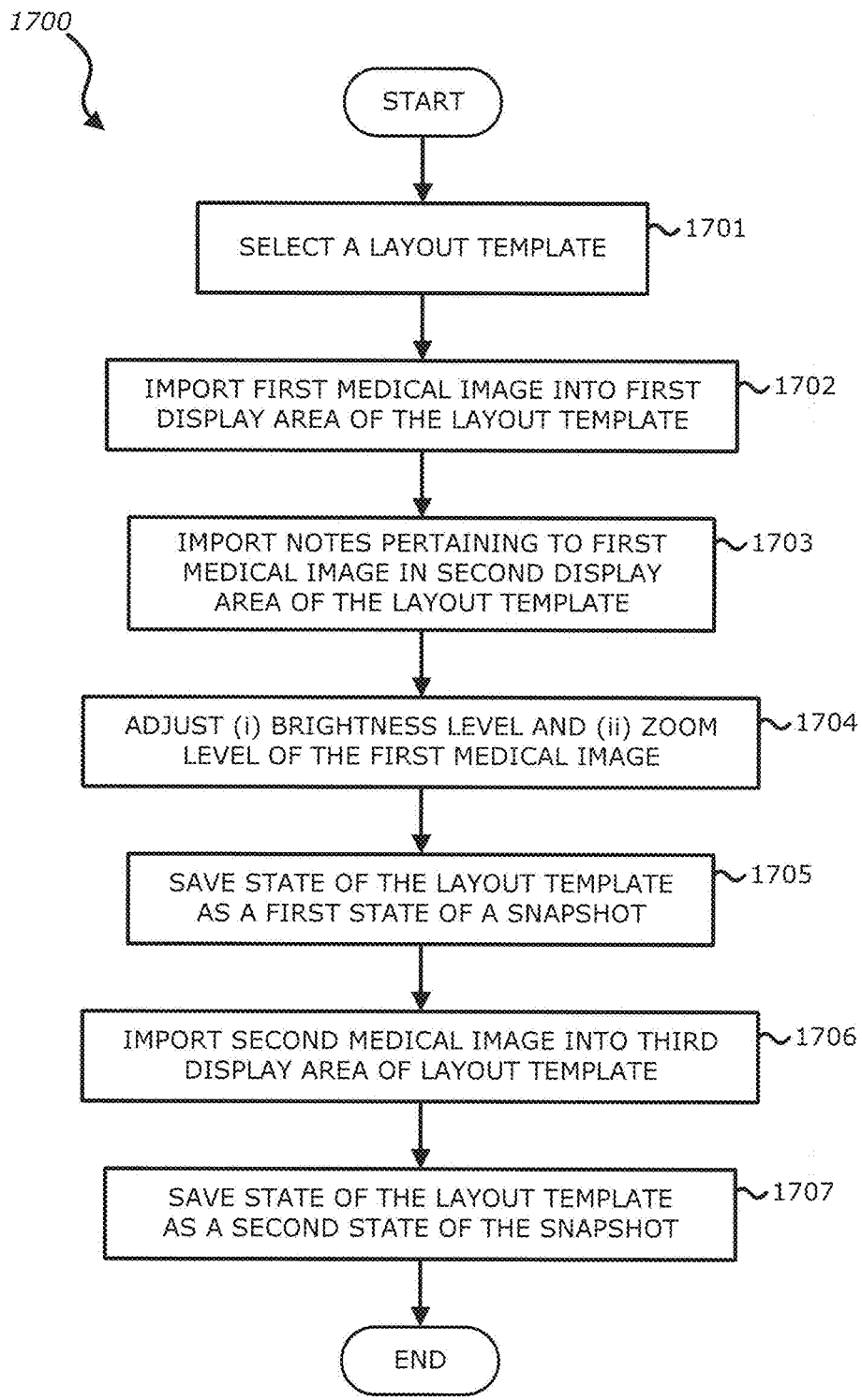
FIG. 17 is a flowchart of an example process of generating a snapshot having a first state and a second state.

Referring to FIG. 17, a flowchart of an example process of generating a snapshot having a first state and a second state is provided. Each block illustrated in FIG. 17 represents an operation performed in the method 1700 of generating a snapshot including a first and second state. At block 1701, a layout template is selected from one or more pre-constructed templates. For example, referring to FIG. 14, a doctor may select one of the layout templates 1411-1416 shown in the display area 1410. Following the selection of a layout template, a first medical image is imported into a first display area of the layout template (block 1702). In one embodiment, the doctor may have taken a plurality of x-ray images of a patient and may select a first x-ray image to import into the layout template. For example, the first x-ray image may show an injury of a patient from a first perspective.

At block 1703, the doctor may import notes pertaining to the imported first medical image in a second display area of the layout template. For example, a doctor may have previously recorded notes while taking the x-ray images. Alternatively, or in addition to, the doctor may enter notes in the second display area while examining the first medical image.

At block 1704, the doctor may adjust one or more viewing properties of the first medical image, such as, among others, (i) a brightness level and/or (ii) a zoom level of the first medical image. In such an example, the doctor may adjust a brightness level in order to more clearly examine the first medical image. In addition, the doctor may increase the zoom level of the medical image in order to focus the examination on a particular portion of the first medical image, e.g., one of a plurality of broken bones suffered during a car accident, wherein the one particular bone will be the focus of a first surgery.

Subsequent to importing the first medical image and notes pertaining to the first medical image (or recording notes during examination of the first medical image) and adjusting one or more viewing properties of the first medical image, the doctor may save the state of the layout template as a first state of a snapshot (block 1705). As discussed above, the doctor may save the state of the layout template such that (i) the specific arrangement of medical images, notes, medical records, etc., is saved and (ii) any adjustments made to the viewing properties (e.g., display attributes) of the medical images are preserved. Therefore, in this example, the adjustment of the brightness level and the zoom level would be perseved. The saved state of the layout template may be referred to as a first state of the snapshot. As discussed above, it is advantageous to save a state of the layout because it is difficult for a doctor to recall the exact steps of obtaining the state from which a conclusion regarding an injury or course of treatment was drawn. Additionally, a saved state of a layout is easy to transmit to a second doctor and/or a nurse or medical technician located remotely compared to transmitting the medical information and instructions as to obtaining the desired state of the layout.

After saving the first state of the snapshot, the doctor may import a second medical image into a third display area of the layout template (block 1706). In one embodiment, a second medical image may be a second perspective of the injury on which the first medical image is focused. Alternatively, the second medical image may be the same x-ray as the first medical image with its viewing properties adjusted differently than the first medical image, an x-ray of a second injury, an x-ray of a second patient having undergone a successful surgery to correct the injury on which the first medical image is focused, etc. Although the method 1700 states that a second medical image is imported into the third display area of the layout template, the doctor may import medical records of the patient of whom the first medical image depicts or other medical information (e.g., treatment or surgery protocol, a timeline for treatment, etc.).

At block 1707, the doctor may then save the state of the layout template as a second state of the snapshot. Having a plurality of saved states may be advantageous as a doctor may use a first state to discuss the injury and potential treatment options with a second doctor or surgeon and use a second state to discuss the injury and potential treatment options with a nurse and the patient as a second doctor or surgeon may not desire to have the additional information that is shown to a nurse or the patient (or vice versa). For example, a second doctor may not want to see an x-ray of a successful surgery to correct the injury but may only need to see one or more perspectives of the actual injury. In the same example, a doctor may find it easier to explain the upcoming surgery to the patient by showing an x-ray of a successful surgery next to an x-ray of the injury (e.g., to explain that a metal plate will be inserted during surgery and what the result will be).

Any combination of the above features and functionalities may be used in accordance with one or more embodiments. In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

We claim:

1. A method comprising:
    accessing a first medical study;
    displaying one or more images from the first medical study in a first display area of a display screen of a user interface, each of the one or more displayed images in a separate relocatable window within the first display area of the display screen;
    receiving one or more user inputs within the first display area, wherein the one or more user inputs cause at least one image of the one or more displayed images to be processed to manipulate an appearance of the at least one image in the separate relocatable window of the at least one image within the first display area of the display screen, wherein manipulating the appearance of the at least one image includes at least one of zooming, panning, or adjusting the brightness of at least one of the one or more images;

receiving one or more user inputs that associate, and display, text with the one or more images;

receiving a user input to add a first selectable entry into a list of one or more entries displayed in a second display area, distinct from the first display area, wherein the first selectable entry records a state of the appearance of all windows opened within the first display area, after processing, of the at least one of the one or more displayed images in a respective window, and records the text associated with the one or more displayed images, wherein a state of appearance of the at least one image in the separate relocatable window includes a location of the separate relocatable window;

adding the first selectable entry to the list in response to receiving a user input, wherein adding the first selectable entry to the list includes recording the state of the manipulated appearance of the at least one image and storing the text in association with the one or more images; and storing the list for future access with the first medical study, wherein a subsequent selection of the first selectable entry causes the one or more images and associated text to be rendered in accordance with the recorded state of the manipulated appearance and arrangement of the windows.

2. The method defined in claim 1 further comprising:
opening a document window within the first display area;
receiving text input into the document window within the first display area;
receiving an input to store a second selectable entry into the list of one or more entries, wherein the second selectable entry stores a state of each window within the first display area, including the document window and text input into the document window within the first display area;
storing the second selectable entry into the list of one or more entries; and
displaying the second selectable entry in the list of one or more entries in the second display area of the display screen.

3. The method defined in claim 1 further comprising:
receiving a selection of an entry in the list; and
displaying a display state recorded with the entry in the first display area or a note recorded with the second display area.

4. The method defined in claim 1 further comprising:
subsequently accessing the first medical study;
obtaining the list from the first medical study;
displaying the list;
receiving a selection of an entry in the list; and
displaying one or both of a display state recorded with the entry in the first display area or a note included in the entry.

5. The method defined in claim 1 further comprising:
issuing a notification;
subsequent to the notification being issued,
accessing the first medical study,
obtaining the list from the first medical study,
displaying the list,
receiving a selection of the first selectable entry in the list, and
displaying a display state recorded with the first selectable entry in the first display area or a note recorded with the second display area.

6. The method defined in claim 5 wherein the notification comprises a request to one or more individuals to review the study and at least a portion of the list.

7. The method defined in claim 5 further comprising:
adding a second selectable entry into the list displayed in a second display area in response to receiving user input; and
storing the list with the first medical study shown in the first display area.

8. The method defined in claim 1 wherein receiving a user input comprises receiving an indication that a user selected a graphical element on a user input display area, the graphical element is a relocatable window containing an image of the first medical study, and the user input relocates the window to at least partially overlap with another relocatable window containing information of the medical study.

9. The method defined in claim 2, wherein at least two images are displayed in the first display area, and each image of the at least two images is displayed in a separate relocatable window, and the appearance of each image is independently modifiable within the separate relocatable window.

10. The method defined in claim 1 wherein the one or more user inputs further comprise at least one of an addition, deletion, or modification to annotations or other graphical elements appearing in the first display area; and
further comprising storing the addition, deletion, or modification to annotations in association or other graphical elements with the first selectable entry and the state of the manipulated appearance in the display screen.

11. The method defined in claim 1 further comprising:
displaying entries of one or more additional studies in the list; and
ordering entries based on entry creation time.

12. The method defined in claim 1 further comprising:
displaying entries of one or more additional studies in the list;
grouping entries displayed in the list based on study; and
ordering entries for each study based on entry creation time.

13. The method defined in claim 1 further comprising assigning a type to one or more log entries.

14. The method defined in claim 1 further comprising:
filtering the list based on type; and
displaying a portion of the list based on a result of filtering the list.

15. The method defined in claim 14 wherein the type comprises a name of an individual.

16. The method defined in claim 1 further comprising:
automatically obtaining measurement data from a remote location, the measurement data relating to the first medical study; and
adding a second entry to the list that includes the display appearance of the first entry and further includes the measurement data.

17. The method defined in claim 1 wherein the list includes a second entry containing procedure information associated with the first medical study, the second entry added to the first medical study when the first medical study was completed.

18. The method defined in claim 1 wherein the list includes a second entry containing report associated with the first medical study, the second entry added to the first medical study when report was in a first state.

19. The method defined in claim 1 further comprising adding a new log entry to the list in response to a document associated with a study being uploaded to a server storing the study, wherein the document is uploaded from the first or second display area and, further comprising opening the document from a new log entry.

20. An electronic system comprising:
one or more processors;
a display screen coupled to the one or more processors;
a network interface coupled to the one or more processors;
a memory coupled to the one or more processors, wherein the memory includes
instructions which when executed by the one or more processors implement logic comprising:
first logic for accessing a first medical study via the network interface;
second logic for displaying one or more images from the first medical study in a first display area of the display screen, wherein each of the one or more images is displayed in a separate relocatable window within the first display area of the display screen;
user interface logic for receiving one or more user inputs within the first display area, wherein the one or more user inputs cause at least one image of the one or more displayed images to be processed to manipulate an appearance of the at least one image in the separate relocatable window of the image within the first area of the display screen, wherein manipulating the appearance of the at least one image includes at least one of zooming, panning, or adjusting the brightness of the at least one image, and user interface logic is configured to receive one or more user inputs that associate, and display, text with the one or more images;
log generation logic for adding a first selectable entry into a list of one or more entries displayed in a second display area, distinct from the first display area, in response to receiving a user input, wherein the first selectable entry records a state of the appearance of the at least one of the one or more displayed images, after processing, in association with the text, and records a state of each window opened within the first display area, and stores the list with the first medical study in the memory, and sends the list for storage via the network interface, wherein a state of the appearance of the at least one image in the separate relocatable window includes a location of the separate relocatable window, wherein a subsequent selection of the first selectable entry causes the one or more images to each be opened and rendered in a respective window in accordance with the recorded state of all opened windows, and associated text to be rendered in accordance with the recorded state of the manipulated appearance of the at least one image and the window to display the image.

21. The system defined in claim 20 wherein the logic further comprises:
the user interface logic is further configured to open a document window within the first display area, receive text input into the document window within the first display area; and
the log generation logic is further configured to receive an input to store a second selectable entry into the list of one or more entries, wherein the second selectable entry stores a state of each window within the first display area, including the document window and text input into the document window within the first display area, wherein the state of each window includes a location of the window;
store the second selectable entry into the list of one or more entries; and
display the second selectable entry in the list of one or more entries in the second display area of the display screen.

22. The system defined in claim 20 wherein the logic further comprises:
user interface logic for receiving a selection of an entry in the list; and
display control logic for displaying a display state recorded with the entry in the first display area or a note recorded with the second display area.

23. The system defined in claim 20 further comprising another electronic device that subsequently accesses the first medical study, obtains the list from the first medical study, displays the list, selects an entry in the list, and displays a display state recorded with the entry in the first display area or a note recorded with the second display area.

24. The system defined in claim 20 wherein the logic further comprises:
issue notification logic for issuing a notification to one or more other individuals to review list and a portion of the first study.

25. The system defined in claim 22 wherein the display control logic includes logic for displaying at least two images in the first display area and each image of the at least two images is displayed within a separate relocatable window, and the appearance of each image is independently modifiable within the separate relocatable window.

26. The system defined in claim 20 wherein the user inputs related to a user's interaction with the first display area further comprise at least one of addition, deletion, or modification to annotations and other graphical elements, including relocating a window containing information of the first medical study appearing in first display area; and
further comprising storing logic that stores the addition, deletion, or modification to annotations and other graphical elements in association with the first selectable entry and the state of the manipulated appearance in the display screen.

27. The system defined in claim 22 wherein the display control logic is operable to display entries of one or more additional studies in the list and order entries based on entry creation time.

28. The system defined in claim 22 wherein the display control logic is operable to display entries of one or more additional studies in the list, group entries displayed in the list based on study; and order entries for each study based on entry creation time.

29. The system defined in claim 22 wherein the display control logic is operable assign a type to the list.

30. The system defined in claim 22 wherein the display control logic is operable to filter the list based on type and display a portion of the list based on a result of filtering the list.

31. The system defined in claim 30 wherein the type comprises a name of an individual.

32. The system defined in claim 20 wherein the logic further comprises:
logic to automatically obtain measurement data from a remote location, the measurement data relating to the first medical study, and wherein the logging logic adds a second entry to the list that includes the display appearance of the first entry and further includes the measurement data.

33. The system defined in claim 20 wherein the list includes a second entry containing procedure information associated with the first medical study, the second entry added to the first medical study when the first medical study was completed.

34. The system defined in claim 20 wherein the list includes a second entry containing report associated with the first medical study, the second entry added to the first medical study when report was in a first state.

35. An article of manufacture having one or more non-transitory storage media storing instruction thereon which, when executed by an electronic system, cause the electronic system to perform a method comprising:
   accessing a first medical study;
   displaying one or more images from the first medical study in a first display area of a display screen of a user interface, each of the one or more displayed images in a separate relocatable window within the first display area of the display screen;
   receiving one or more user inputs within the first display area, wherein the one or more user inputs cause at least one image of the one or more displayed images to be processed to manipulate an appearance of the at least one of the one or more displayed images in the window of the at least one of the one or more displayed images in the first display area of the display screen, wherein manipulating the appearance of the one or more images includes at least one of zooming, panning, or adjusting the brightness of one of the one or more images;
   receiving one or more user inputs that associate and display text with the one or more images;
   receiving a user input to add a first selectable entry to a list of one or more entries displayed in a second display area, distinct from the first display area, wherein the first selectable entry records a state of the appearance of all windows opened within the first display area, after processing, of the at least one of the one or more displayed images, and records the text associated with the one or more displayed images, wherein a state of appearance of the at least one image in the separate relocatable window includes a location of the separate relocatable window;
   adding the first selectable entry into the list in response to receiving a user input, wherein adding the first selectable entry to the list includes recording the state of the manipulated appearance of the one or more displayed images and storing the text in association with the one or more displayed images; and
   storing the list for future access with the first medical study, wherein a subsequent selection of the first selectable entry causes the one or more images and associated text to be rendered in accordance with the recorded state of the manipulated appearance and arrangement of the windows.

36. The article of manufacture defined in claim 35 wherein the method further comprises:
   opening a document window within the first display area;
   receiving text input into the document window within the first display area;
   receiving an input to store a second selectable entry into the list of one or more entries, wherein the second selectable entry stores a state of each window within the first display area, including the document window and text input into the document window within the first display area;
   storing the second selectable entry into the list of one or more entries; and
displaying the second selectable entry in the list of one or more entries in the second display area of the display screen.

37. The article of manufacture defined in claim 35 wherein the method further comprises:
   receiving a selection of an entry in the list from a user; and
displaying a display state recorded with the entry in the first display area or a note recorded with the second display area.

38. The article of manufacture defined in claim 35 wherein the method further comprises:
   subsequently accessing the first medical study;
   obtaining the list from the first medical study;
   displaying the list;
   receiving a selection of an entry in the list from a user; and
   displaying a display state recorded with the entry in the first display area or a note recorded with the second display area.

39. The article of manufacture defined in claim 35 wherein the method further comprises:
   issuing a notification, wherein the notification comprises a request to one or more individuals to review the study and at least a portion of the list; and
   subsequent to the notification being issued,
   accessing the first medical study,
   obtaining the list from the first medical study,
   displaying the list,
   receiving a selection of first selectable entry in the list from a user, and
displaying a display state recorded with the first selectable entry in the first display area or a note recorded with the second display area.

* * * * *